US011866772B2

(12) United States Patent
Tai et al.

(10) Patent No.: US 11,866,772 B2
(45) Date of Patent: Jan. 9, 2024

(54) DIGITAL PCR FOR NON-INVASIVE PRENATAL TESTING

(71) Applicant: Roche Molecular Systems, Inc., Pleasanton, CA (US)

(72) Inventors: Yu Chuan Tai, Pleasanton, CA (US); Nancy Schoenbrunner, Moraga, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1002 days.

(21) Appl. No.: 16/790,509

(22) Filed: Feb. 13, 2020

(65) Prior Publication Data

US 2020/0181693 A1 Jun. 11, 2020

Related U.S. Application Data

(62) Division of application No. 14/493,271, filed on Sep. 22, 2014, now Pat. No. 10,612,080.

(51) Int. Cl.
| | |
|---|---|
| *C12Q 1/6851* | (2018.01) |
| *G16B 20/00* | (2019.01) |
| *G16H 50/30* | (2018.01) |
| *G16B 20/10* | (2019.01) |

(52) U.S. Cl.
CPC .......... *C12Q 1/6851* (2013.01); *G16B 20/00* (2019.02); *G16B 20/10* (2019.02); *G16H 50/30* (2018.01); *C12Q 2600/156* (2013.01)

(58) Field of Classification Search
None
See application file for complete search history.

(56) References Cited

U.S. PATENT DOCUMENTS

| | | |
|---|---|---|
| 2013/0178373 A1 | 7/2013 | Rabinowitz et al. |
| 2013/0260381 A1 | 10/2013 | Ramakrishnan |

FOREIGN PATENT DOCUMENTS

| | | |
|---|---|---|
| CN | 103911427 A | 7/2014 |
| WO | 2013/072069 A1 | 5/2013 |
| WO | 2014/043581 A1 | 3/2014 |

OTHER PUBLICATIONS

Dube, S. et al.; "Mathematical Analysis of Copy Number Variation in a DNA Sample Using Digital PCR on a Nanofluidic Device"; *PLOS ONE*; vol. 3, No. 8; Aug. 6, 2008; pp. 1-9.
Fan, C. et al.; "Detection of Aneuploidy with Digital Polymerase Chain Reaction"; *Analytical Chemistry*; American Chemical Society, US, vol. 79, No. 19; Oct. 1, 2007; pp. 7576-7579.
Fan, C. et al.; "S-1 Supporting Information 'Detection of Aneuploidy with Digital PCR'"; *Analytical Chemistry*; Aug. 24, 2007.
Gu, K. et al.; "Testing the Ratio of Two Poisson Rates"; *Biometrical Journal*; vol. 50, No. 2; Mar. 3, 2008; pp. 283-298.
Heyries, K.A. et al.; "Megapixel digital PCR"; *Nature Methods*; vol. 8, No. 8; Jul. 3, 2011; pp. 649-651 and Supplementary Notes.
Huffman, M.D.; An improved approximate two-sample poisson test; *Journal of the Royal Statistical Society*; Series C (Applied Statistics); vol. 33; pp. 224-226, 1984.
Huggett, J.F. et al.; "Guidelines for Minimum Information for Publication of Quantitative Digital PCR Experiments"; *Clinical Chemistry*; vol. 59, No. 6; Jun. 2013; pp. 892-902.
Kreutz, J.E. et al.; "Theoretical design and analysis of multivolume digital assays with wide dynamic range validated experimentally with microfluidic digital PCT"; *Analytical Chemistry*; American Chemical Society, US; vol. 83, No. 21; Nov. 1, 2011; pp. 8158-8168.
Lo, Y. M.D. et al.; "Digital PCR for the Molecular Detection of Fetal Chromosomal Aneuploidy"; *Proceedings of the National Academy of Sciences of the United States of America*; vol. 104, No. 32; Aug. 7, 2007; pp. 13116-13121.
Lun, F.M.F. et al.; Noninvasive prenatal diagnosis of monogenic diseases by digital size selection and relative mutation dosage on DNA in maternal plasma; *Proceedings of the National Academy of Sciences*, vol. 105, No. 50; pp. 19920-19925; 2008.
Mallona, I. et al.; "pcrEfficiency: a Web tool for PCR amplification efficiency prediction"; *BMC Bioinformatics*; vol. 12; p. 404; 2011.
Ng, H.K.T. et al.; "Testing the equality of two poisson means using the rate ratio"; *Statistics in Medicine*, vol. 24; pp. 955-965; 2005.
Ruijter, J.M. et al.; "Evaluation of qPCR curve analysis methods for reliable biomarker discovery: Bias, resolution, precision, and implications"; Methods 59; pp. 32-46; 2013.
Sanders, R. et al.; "Evaluation of Digital PCR for Absolute DNA Quantification"; *Analytical Chemistry*; vol. 83, No. 17; Sep. 1, 2011; pp. 6474-6484.
Stevenson, C.L.; "The Statistics of Measurements: Chapter 3: Measurements as Random Variables"; Jan. 1, 2000; retrieved from the internet on Jan. 9, 2014; https://facultystaff.richmond.edu/rdominey/300/local/Ch3.PDF.
Whale, A. S. et al.; "Methods for Applying Accurate Digital PCR Analysis on Low Copy DNA Samples"; PLOS ONE; vol. 8, No. 3; Mar. 5, 2013; pp. 1-10.
Whale, A.S. et al.; "Comparison of microfluidic digital PCR and conventional quantitative PCR for measuring copy number variation"; Nucleic Acids Research; vol. 40, No. 11; Feb. 28, 2012; pp. 1-9.

(Continued)

*Primary Examiner* — Joseph Woitach
(74) *Attorney, Agent, or Firm* — Kilpatrick Townsend and Stockton LLP

(57) ABSTRACT

Techniques are provided for determining settings of a dPCR experiment for the detection of a chromosomal aneuploidy in a plasma sample from a female pregnant with a fetus. Data about the sample, the dPCR process, and a desired accuracy can be used to determine the settings. Such settings can include a minimal input number of control chromosome molecules for the dPCR experiment, a minimal number of control chromosome molecules for a pre-amplification procedure, and a number of PCR cycles in the pre-amplification procedure. These settings can be used to satisfy the accuracy specified by the accuracy data. Thus, the dPCR experiment can be designed to achieve the desired accuracy while reducing cost, e.g., by not using more of a sample than needed and not performing more pre-amplification than needed or performing more manipulations than needed.

13 Claims, 11 Drawing Sheets

(56) References Cited

OTHER PUBLICATIONS

Zimmermann, B.G. et al.; "PCR: a powerful new tool for noninvasive prenatal diagnosis?" Prenatal Diagnosis, vol. 28, No. 12; pp. 1087-1093; 2008.

| FP | FN | Min # Molecules 3% fetal | Min # Molecules 5% fetal | Min # Molecules 10% fetal | Min # Molecules 15% fetal |
|---|---|---|---|---|---|
| 0.01 | 0.01 | 194590 | 70573 | 17970 | 8132 |
| 0.025 | 0.025 | 138123 | 50094 | 12755 | 5772 |
| 0.05 | 0.01 | 141851 | 51468 | 13119 | 5943 |

FIG. 6

| Number of Loci | FP | FN | Min_PCR_Cycles (3% fetal) | Min_PCR_Cycles (5% fetal) | Min_PCR_Cycles (10% fetal) | Min_PCR_Cycles (15% fetal) |
|---|---|---|---|---|---|---|
| 1 | 0.01 | 0.01 | 10 | 10 | 9 | 8 |
| 1 | 0.025 | 0.025 | 10 | 9 | 8 | 8 |
| 1 | 0.05 | 0.01 | 10 | 9 | 8 | 8 |
| 12 | 0.01 | 0.01 | 7 | 6 | 5 | 5 |
| 12 | 0.025 | 0.025 | 6 | 6 | 5 | 4 |
| 12 | 0.05 | 0.01 | 6 | 6 | 5 | 4 |
| 96 | 0.01 | 0.01 | 4 | 3 | 2 | 1 |
| 96 | 0.025 | 0.025 | 3 | 2 | 1 | 1 |
| 96 | 0.05 | 0.01 | 3 | 2 | 2 | 1 |

FIG. 7

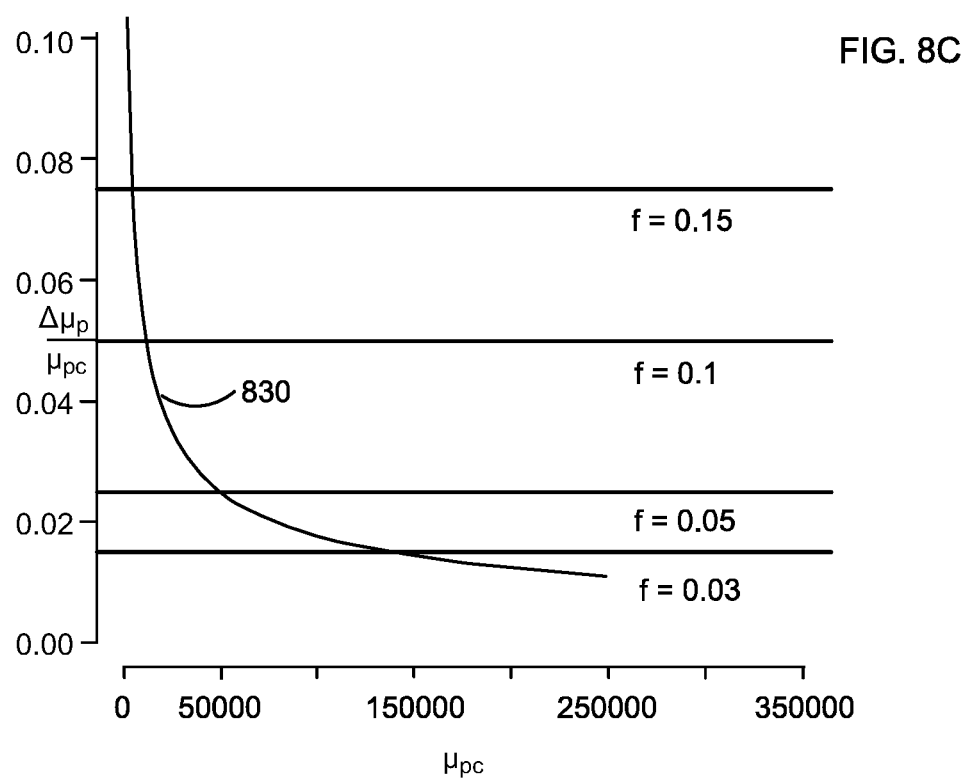

DIGITAL PCR FOR NON-INVASIVE PRENATAL TESTING

CROSS REFERENCES TO RELATED APPLICATIONS

The present application is a divisional application of U.S. patent application Ser. No. 14/493,271, filed on Sep. 22, 2014, which application is incorporated herein by reference in its entirety.

FIELD

This disclosure is generally related to digital PCR, and more specifically to designing a digital PCR experiment (e.g., determining a number of pre-amplification cycles) for performing non-invasive prenatal testing.

BACKGROUND

Digital PCR (dPCR) is a simple, rapid, yet accurate technology for non-invasive prenatal testing ([1], [2], [3], [4]). However, there has not been any well-established statistical tool for designing a dPCR experiment in this application. Some existing methods (e.g. [1] and [7]) have not considered important quantities specific in this application.

For example, reference [1] provides a method to estimate number of partitions assuming the proportion of positive compartment is $\frac{1}{3}$ in order to detect aneuploidy at 5% false positive rate. Among other things, their method does not consider false negative rate, and does not consider a pre-amplification step. Reference [7] provides a formula for dPCR precision (minimum difference in concentration that can be reliably detected with less than 1% false positive and less than 1% false negative.). Their context is in SNV detection and copy number difference, and they do not consider fetal fraction. They do not consider a pre-amplification step either.

Accordingly, improved systems and methods for designing a dPCR experiment for prenatal testing are needed.

BRIEF SUMMARY

Embodiments of the present invention provide techniques for determining settings of a dPCR experiment for the detection of a chromosomal aneuploidy in a plasma sample from a female pregnant with a fetus. Data about the sample, the dPCR process, and a desired accuracy can be used to determine the settings. Such settings can include a minimal input number of control chromosome molecules for the dPCR experiment, a minimal number of control chromosome molecules for a pre-amplification procedure, and a number of PCR cycles in the pre-amplification procedure. These settings can be used to satisfy the accuracy specified by the requirements for the application. Thus, the dPCR experiment can be designed to achieve the desired accuracy while reducing cost, e.g., by not using more of a sample than needed and not performing more pre-amplification than needed.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 6 is a table showing minimal input number of control chromosome molecules required for a dPCR experiment in order to detect T21 according to embodiments of the present invention.

FIG. 7 is a table showing minimal number of PCR cycles required for a pre-amplification in order to achieve the minimal number of control chromosome molecules input to a dPCR experiment (FIG. 6) from the minimal number of control chromosome molecules input to a pre-amplification (FIG. 5) according to embodiments of the present invention.

FIGS. 8A-8C show the relationship between minimal detectable relative difference in expected numbers of molecules $\Delta\mu_p/\mu_{pc}$ (black solid line) and number of control chromosome molecules $\mu_{pc}$ for different levels of FP and FN rates. The color lines are relative difference in expected numbers of molecules under different fetal fractions.

DEFINITIONS

Figure 1:
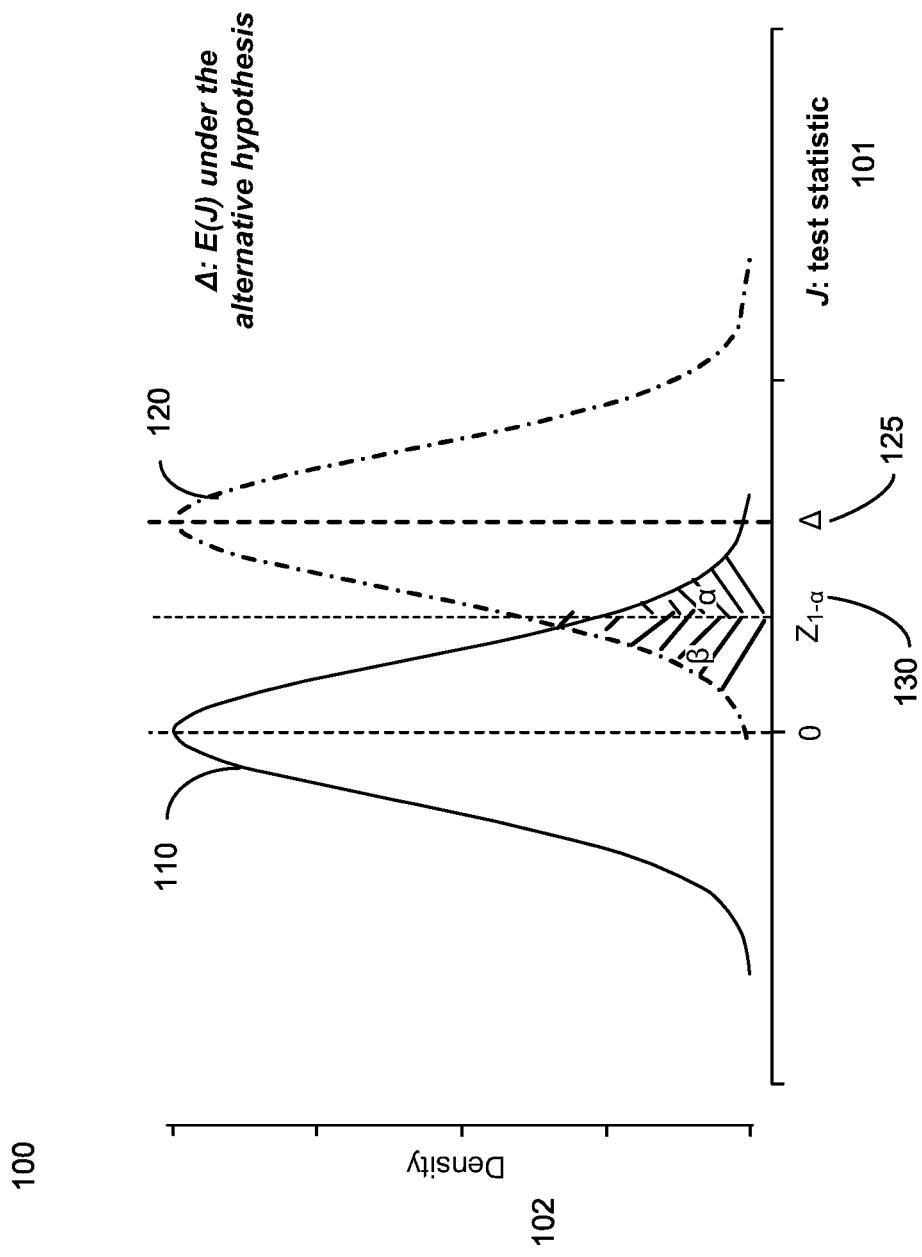
FIG. 1 shows a diagram 100 of the distribution of the test-statistic when the test sample is normal, and when the test sample is aneuploidy according to embodiments of the present invention.

The relative difference in expected numbers of molecules quantifies on average how many more aneuploid chromosome molecules than normal chromosome molecules in a patient's plasma (containing a certain fraction of cell-free fetal DNA) are input to a dPCR experiment after a pre-amplification based on specified input variables. The relative difference can depend on various values, such as the fetal DNA fraction and the degree of aneuploidy.

The minimal detectable relative difference in expected numbers of molecules corresponds to a relative difference in expected number of DNA molecules between an aneuploid chromosome and a normal chromosome after a pre-amplification that can reliably be detected within specified false positive and false negative rates. The difference can include a multiplier as a result of a different number of loci on a chromosome relative to the other chromosome.

The test statistic is a quantity calculated based on the observed data to measure how much evidence the observed data provide against the null hypothesis that the test chromosome is normal. Examples of a test statistic include a difference or a ratio of the number of molecules from the test chromosome and the control chromosome.

The number of molecules input to a pre-amplification corresponds to the number of haploid genomes in the maternal plasma input to a pre-amplification. The input DNA volume can determine this number, even though fragmented small pieces of cell-free DNA are in the plasma. The number of cell-free DNA at each locus before a pre-amplification is the same as the number of molecules input to a pre-amplification. The more loci for a pre-amplification, the more cell-free DNA input to a pre-amplification, even though the input number of molecules to a pre-amplification stays the same. The minimal number of molecules corresponds to the minimal number of molecules at each locus, assuming the numbers of molecules across loci are the same. Therefore, the more loci, the more input molecules.

The number of molecules input to a dPCR experiment corresponds to the number of cell-free DNA generated from a pre-amplification and input to a dPCR experiment. This is different from the input number of molecules to a pre-amplification.

DETAILED DESCRIPTION

Embodiments provide a statistical framework for designing a digital polymerase chain reaction (dPCR) experiment for non-invasive prenatal testing. Such prenatal testing uses cell-free DNA from the fetus, which can be found in a sample from the pregnant female. For example, cell-free fetal DNA can be found in maternal plasma.

A key difference between a dPCR experiment's application in non-invasive prenatal testing and other dPCR applications is that cell-free fetal DNA is very limited in the former setting. In order to reach the power for detecting the small difference between an aneuploid chromosome and a normal chromosome, embodiments perform a pre-amplification on the chromosomes under study at multiple loci before a dPCR experiment is conducted. Embodiments can be used to determine particular settings for a dPCR experiment to provide a desired accuracy. Example settings can include an amount of maternal sample to use (e.g., as determined by a minimal number of control chromosome molecules for a pre-amplification procedure), a number of pre-amplification cycles, and an amount of DNA to be input to the dPCR experiment (e.g., as determined by a minimal input number of control chromosome molecules for the dPCR experiment).

I. INTRODUCTION

Embodiments perform a pre-amplification before the actual dPCR experiment. In a simple example using one locus and a small maternal sample (for illustration purposes), suppose the maternal sample had 100 DNA molecules from a first locus on chromosome 1 and 105 DNA molecules from a second locus on chromosome 21 (5% cell-free fetal DNA). In a normal sample, the number of DNA molecules should be equal, with some measurement variability. Here, the difference is five DNA molecules, which can be difficult to detect.

These 205 DNA molecules can be input to a pre-amplification procedure to obtain 79496.15 DNA molecules from the first locus, and 83470.96 DNA molecules from the second locus (assuming PCR efficiency of 0.95 and 10 PCR cycles for both chromosomes during the pre-amplification). The difference is now 3974.81 DNA molecules, which can be easier to detect.

Multiple loci can not only be used to obtain desired amounts of DNA molecules with fewer PCR cycles, but also can average out the imbalance in PCR efficiencies and fetal fractions across loci. This can be important, since the amounts of cell-free fetal DNA is limited. And, in order to detect an aneuploidy with the desired power, one has to input enough molecules. Furthermore, the dPCR experiment should be designed in a careful manner to obtain the desired accuracy, e.g., as defined by error rate criteria, such as false positive rates and false negative rates. And, one does not want to perform too many pre-amplification cycles, as it would introduce too much PCR noise such as amplification imbalance or misincorporations.

A. Digital PCR Experiment with Pre Amplification

One challenge of a pre-amplification is that when sampling a portion of plasma of very low fetal fraction into a pre-amplification, the standard error of fetal fraction of the sampled plasma could be quite large. It is necessary to make sure the input number of molecules to a pre-amplification is large enough so that the fetal fraction in the sampled plasma is precise enough.

Embodiments can address the following points: (1) What is the minimal detectable relative difference in expected numbers of molecules between an aneuploid chromosome and a normal chromosome input to a dPCR experiment and how many control chromosome molecules in total one has to input to a dPCR experiment in order to detect an aneuploidy reliably at certain levels of false positive and false negative rates? (2) How many molecules in total one has to input to a pre-amplification in order to control fetal fraction standard error at a tolerable level? (3) How many PCR cycles is required for the pre-amplification?

Embodiments can address these questions by first calculating the relative difference in expected numbers of molecules between an aneuploid chromosome and a normal chromosome after a pre-amplification. In one implementation, this relative difference in expected numbers of molecules incorporates a fetal DNA fraction in the biological sample, number of PCR cycles, and PCR amplification efficiencies. In one embodiment, one can assume that the average PCR efficiencies of the test and control chromosomes are the same, and thus PCR cycle number and PCR efficiencies are not needed to estimate the input number of molecules to a dPCR experiment.

The relative difference in expected numbers of molecules can be used to estimate the minimal detectable relative difference in expected numbers of molecules, which is a minimal difference in DNA molecules from one chromosome relative to the other chromosome, where this minimal relative difference can reliably be detected at specified levels of false positive and false negative rates. A variance stabilizing transformation test statistic can be used to determine this difference.

The relative difference in expected numbers of molecules can be used to provide the minimal total number of molecules required for a dPCR experiment in order to detect an aneuploidy at specified levels of false positive and false negative rates. Embodiments can further provide a way to estimate the required total number of molecules input to a pre-amplification in order to control the standard error in the fetal DNA fraction at a tolerable level.

Given the minimal total number of molecules required to input to a dPCR experiment and the total number of molecules required to input to a pre-amplification, embodiments can estimate the required number of PCR cycles for a pre-amplification. Results (provided below) show that it is possible to detect an aneuploidy at 1% false positive and 1% false negative rates, even at a fetal fraction as low as 3%. The lower the fetal fraction, the more total number of molecules is required to input to a pre-amplification. The more stringent the false positive and false negative rates or the lower the fetal fraction, the more total number of molecules is required to input to a dPCR experiment in order to detect an aneuploidy. At a certain number of molecules input to a dPCR experiment, the higher the fetal DNA fraction, the more likely it is able to detect an aneuploidy. The more the number of loci for a pre-amplification, the fewer the number of PCR cycles is required.

B. Test Statistic

When a sample is analyzed to determine whether or not a fetal aneuploidy exists, a test statistic is obtained for the sample. The test statistic is a quantity calculated from the dPCR output data of this sample measuring the amounts of evidence that the test chromosome is aneuploid. For example, the test statistic can be determined using a first number of DNA molecules from the test chromosome and a second number of DNA molecules from one or more control chromosomes. The test statistic can then be compared to a cutoff value to classify the sample, e.g., to classify as aneuploid or normal, or potentially unclassified when two cutoff values are used. An example of a test statistic is a difference or ratio. When a difference is used, a normalization can be performed such that the test statistic incorporates the standard error of the difference.

The choice of the cutoff affects the false positive and false negative rates. In an example where one cutoff value is used, a larger cutoff value will reduce the false positive rate, but will increase the false negative rate. And, a lower cutoff value will reduce the false negative rate, but will increase the false positive rate.

Two cutoff values can be used, where a first cutoff is less than a second cutoff. For example, if the test statistic is lower than a first cutoff, then the sample can be identified as normal. If the test statistic is higher than a second cutoff, then the fetus can be identified as having an aneuploidy. If the test statistic is between the first cutoff and the second cutoff, then the sample can be indeterminate. If the first cutoff is made lower to reduce false negatives and/or the second cutoff value is increased to reduce false positives, the number indeterminate samples increases, which is also a problem. A description of a particular test statistic and error rates is now described.

FIG. 1 shows a diagram 100 of distribution of a test-statistic for normal samples and aneuploid samples according to embodiments of the present invention. The horizontal axis 101 corresponds to different values for the test statistic J. The vertical axis 102 corresponds to the proportion of times a particular test statistic is observed, and is labeled as density. In this example, the statistic J corresponds to a difference between a test number of test molecules (i.e., from the test chromosome) and a control number of control molecules (i.e., from a control chromosome), standardized by the standard error of this difference. Thus, in this example of using one control chromosome, a normal sample would be expected to have a test statistic value of zero, since a number of DNA molecules should be the same. An aneuploid sample would be expected to have a higher value for test statistic J.

Distribution 110 shows the probability distribution of the test statistic for normal samples. Due to natural variations regarding which DNA molecules happened to be in the sample, some normal samples will have more or less test molecules than control molecules. But, the most likely value is zero, which is at the peak of probability distribution 110. The distributions follow a normal distribution and are presented here for illustration.

Distribution 120 shows the probability distribution of test statistic for aneuploid samples. The peak of distribution 120 corresponds to Δ 125. The value of Δ 125 is dependent on the number of molecules in the experiment. The more molecules input to a dPCR experiment, the larger the Δ. The value of Δ 125 is also dependent on the fetal DNA fraction in the sample. When the fetal DNA fraction is larger, there are more test molecules (i.e., because these samples have aneuploidy), and the test statistic has a larger value.

In diagram 100, the cutoff value 130 is used to show false positive rate α and false negative rate β. The values of distribution 110 that are greater than cutoff value 130 would be incorrectly classified as having an aneuploidy, and thus are false positives Values of distribution 120 that are less than cutoff value 130 would be incorrectly classified as being normal, and thus are false negatives.

Accordingly, to control the false positive rate to be no larger than α, embodiments can reject the null hypothesis if J is larger than cutoff 130, labeled as $z_{1-\alpha}$. Under the alternative hypothesis (i.e., an aneuploidy), test statistic J has a normal distribution with mean Δ and standard deviation 1, for this example. Given the cutoff value $z_{1-\alpha}$, the false negative rate is no larger than β. In other words, the power is at least 1–β. The number of input control chromosome molecules will affect Δ. That is, the more molecules, the further away Δ is from 0. Thus, the more molecules, there is less overlap between distributions 110 and 120, and the lower the false negative rate. In some embodiments, since J is a variance stabilizing test statistic, the width of the two normal curves stay constant even when the number of molecules increases.

As one can see, the choice of cutoff value 130 dictates false positive rate and false negative rate. One way to reduce the false-negative rate is to increase the number of molecules input to a dPCR experiment, as this would increase Δ 125. The widths of distributions 110 and 120 would stay the same, thus the amount of overlap of the two distributions would decrease, and the false negative rate would decrease. However, a larger number of molecules for the experiment incurs additional cost and time. Embodiments can determine a minimum number of input molecules for the dPCR experiment to achieve desired error rates. This memo value can be used to minimize time and cost while achieving the desired error rates.

In one embodiment, a test number of DNA molecules from test chromosome 21 (other test chromosomes can be used) after a pre-amplification of p PCR cycles is labeled as $W_{p21}$ and a control number of DNA molecules from the control chromosome is labeled $W_{pc}$. A single-volume dPCR experiment corresponds to when all partitions of the dPCR instrument have the same volume. A multi-volume dPCR experiment corresponds to when partitions are of different volumes.

For single-volume dPCR experiments, in some embodiments, a Poisson correction can be performed. The estimated total numbers of molecules $W_{p21}$ and are $W_{pc}$ calculated using the Poisson equation: $W_{p21}=-N \log(1-q_{21})$ and $W_{pc}=-N \log(1-q_c)$, where $q_{21}$ and $q_c$ are the proportions of positive partitions in the chromosome 21 and control chromosome channels, respectively, for a particular dPCR experiment, and where N is the total number of partitions. These two proportions can be calculated using any approach dividing partitions in each channel into positive and negative ones.

In one embodiment, to calculate $q_{21}$ and $q_c$, clustering can be performed on the intensities of all the partitions in a 2-dimensional space, and the numbers of positive partitions in both channels is counted. These counts can be divided by the total number of partitions N. For multi-volume dPCR experiments, they can be estimated by solving equation (8) in reference [11] for the estimated numbers of chromosome 21 and control chromosome molecules per mL $\hat{\lambda}_{p21}$ and $\hat{\lambda}_{pc}$, respectively, and convert these concentrations to $W_{p21}$ and $W_{pc}$ using the following equations:

$$W_{p21} = \sum_{i=1}^{m} n_i v_i \hat{\lambda}_{p21} \text{ and } W_{pc} = \sum_{i=1}^{m} n_i v_i \hat{\lambda}_{pc},$$

where as defined in reference [11], $v_i$ is the i-th well volume (mL), $n_i$ is the number of partitions at well volume $v_i$ and m is the total number of different well volumes.

C. Measuring Fetal DNA Fraction

As mentioned above, the fetal DNA fraction will affect the number of test DNA molecules on the test chromosome when the fetus has an aneuploidy. The fetal DNA fraction can be measured in a variety way, e.g., as described below. The measurement will have a certain degree of error, which can affect the desired false negative rate, since an overestimated fetal fraction results in insufficient amounts of input DNA molecules to the dPCR experiment. Such an overestimation will move the expectation value Δ toward 0, and thus will increase the false negative rate, in the example above.

An under-estimated fetal fraction will result in more molecules than necessary to input to the dPCR experiment, and thus will lead to a lower false negative rate but higher experimental cost. Thus, instead of measuring fetal fraction, one may simply use a lower bound for fetal fraction to ensure enough statistical power to detect an aneuploidy when enough resources are available. Embodiments can account for an error tolerance in the measurement of the fetal DNA fraction, e.g., in order to determine a minimal number of control DNA molecules for the pre-amplification procedure.

Fetal DNA fraction is typically measured by using a genetic marker that is present only on fetal DNA, but not on maternal DNA, to differentiate fetal from maternal molecules. A portion of extracted mother's plasma is amplified, usually before the pre-amplification, using s PCR cycles on at least one locus containing the genetic marker specific to the fetus and at least one marker common to both fetus and mother The fetal DNA marker can be used to count fetal DNA molecules and the common locus can be used to count total DNA molecules, and thus the ratio of fetal DNA count divided by total DNA count provides the fetal DNA fraction. A factor of two can also be introduced to account for one fetal allele being the same as the maternal allele at the locus.

There are two different types of fetal markers that can be used for this approach. The first is to utilize an epigenetic marker that is present in a specific form only for fetal DNA. The epigenetic marker can be biochemically converted to a differentially amplifiable form, such that a specific primer sequence only amplifies the DNA that was originally either non-methylated or methylated. An example includes treatment with sodium bisulfite which converts non-methylated dC residues to dU. Another type of marker that can be used for this approach to measure fetal fraction is only for male pregnancy. When the fetus is male, one can use chromosome Y to measure the number of fetal molecules.

Figure 2B:
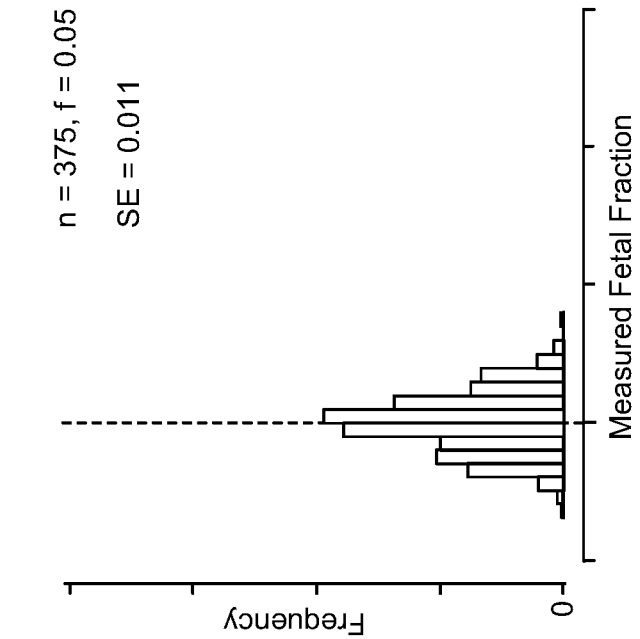
FIGS. 2A-2C illustrate the impact of the number of input control chromosome molecules to a pre-amplification procedure upon the standard error of the estimated fetal fraction according to embodiments of the present invention.
Figure 2A:
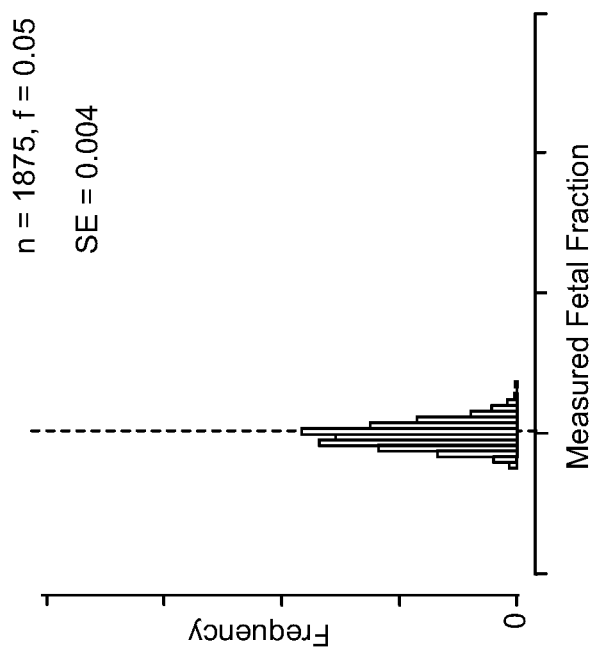
Figure 2C:
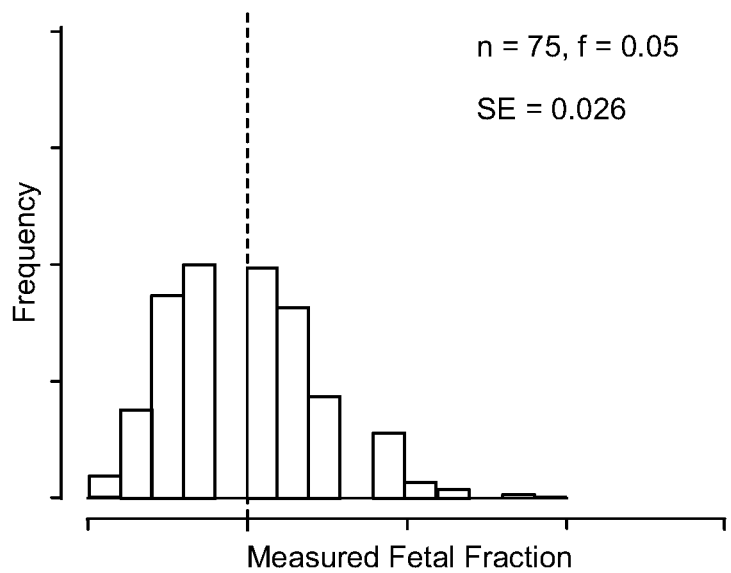

FIGS. 2A-2C illustrate the impact of the number of input control chromosome molecules to a pre-amplification procedure upon the standard error of the fetal fraction in the input plasma according to embodiments of the present invention. A simulation was performed to show how number of input control chromosome molecules to a pre-amplification affects the standard error of fetal fraction.

Suppose the whole plasma extracted from a patient is 100 µl containing 7500 control chromosome molecules, and 5% of these molecules are fetal DNA. Suppose we sample 3 different portions of the whole plasma for the pre-amplification: 25 µl, 5 µl, and 1 µl, containing 1875, 375, and 75 molecules in total, respectively. The subsamples are drawn randomly 1000 times for each volume. The distributions of the fetal fraction for these 3 different volumes are plotted in FIGS. 2A-C, where FIG. 2A corresponds to 25 µl, FIG. 2B corresponds to 5 µl, and FIG. 2C corresponds to 1 µl. FIG. 2A-2C show that the more molecules sampled, the smaller the standard error of the fetal fraction. Thus, a higher number of DNA molecules in the sample provides a more accurate fetal fraction.

Figure 2D:
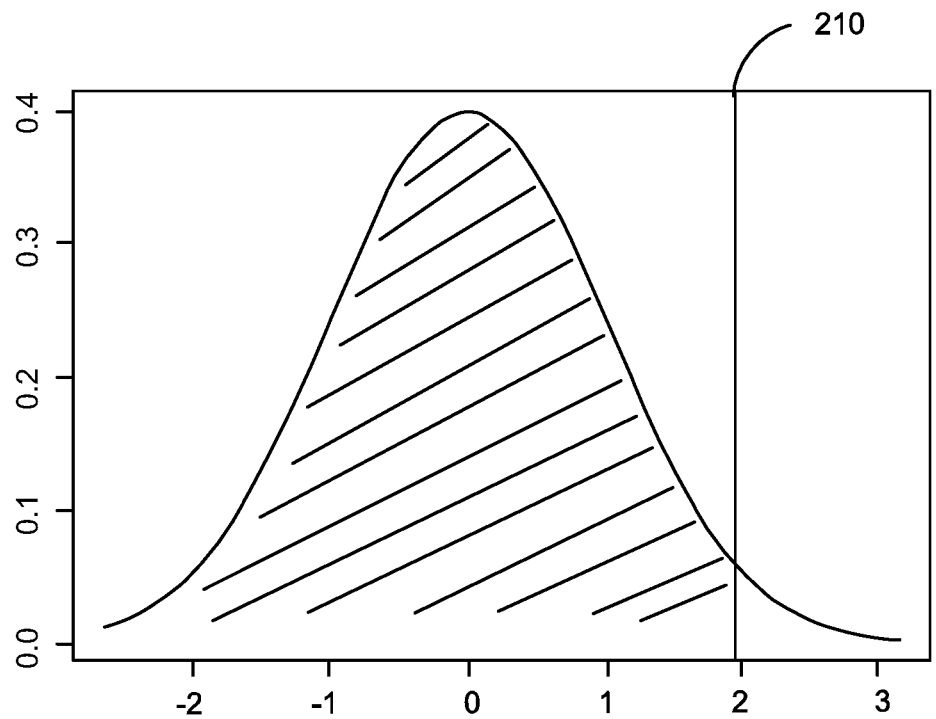
FIG. 2D illustrates the 97.5% th quantile of the standard Normal distribution.

FIG. 2D shows a plot of a normal distribution that relates to accuracy of the fetal DNA fraction. The error control number (labeled η herein) controls the probability that the relative error is within a certain level of tolerance. The value $$z_{1-\frac{\eta}{2}}$$

(210) in equation (32), described below, is the $$100\left(1 - \frac{\eta}{2}\right) \% \text{ th}$$

quantile of the standard Normal distribution. For example, if η=0.05, then $$z_{1-\frac{\eta}{2}}$$

is the 97.5% th quantile of the standard Normal distribution, which is 1.96 in FIG. 2D.

In general, a x % quantile of the standard Normal distribution is a value at which the area under the bell shaped curve from the left and up to this point is x %. The error control number η controls the probability that the relative error between the unknown true (expected) fetal fraction in the whole plasma and the fetal fraction from the sampled plasma within a certain level of tolerance. The error control number η can be set by the user, and will impact the minimal number of DNA molecules to input to the pre-amplification procedure, such that the probability that the fetal DNA fraction is within the error tolerance is satisfactory. Example values of the error control number η are 0.01, 0.05, and 0.1.

II. OBTAINING SETTINGS

A dPCR experiment can be defined by various settings. One setting is the number of DNA molecules for a pre-amplification procedure. This number of DNA molecules can be defined with respect to a number of control DNA molecules from a control chromosome(s). Another setting is a number of cycles (e.g., PCR cycles) in the pre-amplification procedure. Another setting is a minimal input number of DNA molecules for the dPCR experiment. This number of DNA molecules can also be defined with respect to a number of control DNA molecules from a control chromosome(s).

A. Inputs

Various data can be used to determine the settings of the dPCR experiment. For example, data about the sample can be used. Such sample data can include a fetal DNA fraction measured in the plasma sample. The fetal DNA fraction affects the amount of molecules from the control chromosome(s) relative to the amount of molecules from the test chromosome, and thus affects a minimal number of molecules needed. The higher the fetal fraction, the larger the difference between the control and test chromosomes, and the fewer the number of molecules are needed.

Data about the physical process of the dPCR experiment can also be used. Such process data can include a number of loci on each of a test chromosome and one or more control chromosomes. Below are examples of dPCR process data. The number of loci corresponds to the number of loci that are amplified in the pre-amplification step, which affects the number of pre-amplification cycles to obtain the minimal control molecules for input to the dPCR experiment. Data about PCR efficiencies for the pre-amplification procedure can affect the number of PCR cycles. Such data can take various forms, such as: a pre-specified lower bound for PCR efficiencies, an assumption about equal average PCR efficiencies of the test chromosome and the control chromosome, and PCR efficiency rates for the pre-amplification procedure for a test chromosome and a control chromosome.

As another example of process data, the degree of aneuploidy being tested by the dPCR experiment affects the relative difference in expected numbers between normal and the aneuploidy being tested (e.g., a larger difference would be expected for tetrasomy than for trisomy). Additionally, a portion constraint can specify a portion of DNA molecules resulting from a pre-amplification procedure to be input to the dPCR experiment. The higher the portion of DNA molecules from the pre-amplification procedure being used, the fewer pre-amplification cycles are needed to obtain the minimal number of molecules.

Data about desired accuracy of the dPCR experiment can also be used. The desired accuracy can be determined based on external requirements (e.g., regulatory requirements) or internal requirements. As examples, the accuracy data include a fetal DNA fraction error tolerance in a measurement of the fetal DNA fraction. A larger error tolerance leads to fewer control chromosome molecules that are needed for the pre-amplification procedure. An error control number can control a probability that a relative error between an unknown expected fetal DNA fraction and an estimated fetal DNA fraction from the plasma is within the fetal DNA fraction error tolerance. A smaller error control number requires more control chromosome molecules that are needed for the pre-amplification procedure. The accuracy data can also include error rate criteria (e.g., a false positive rate and a false negative rate).

B. Method

Figure 3:
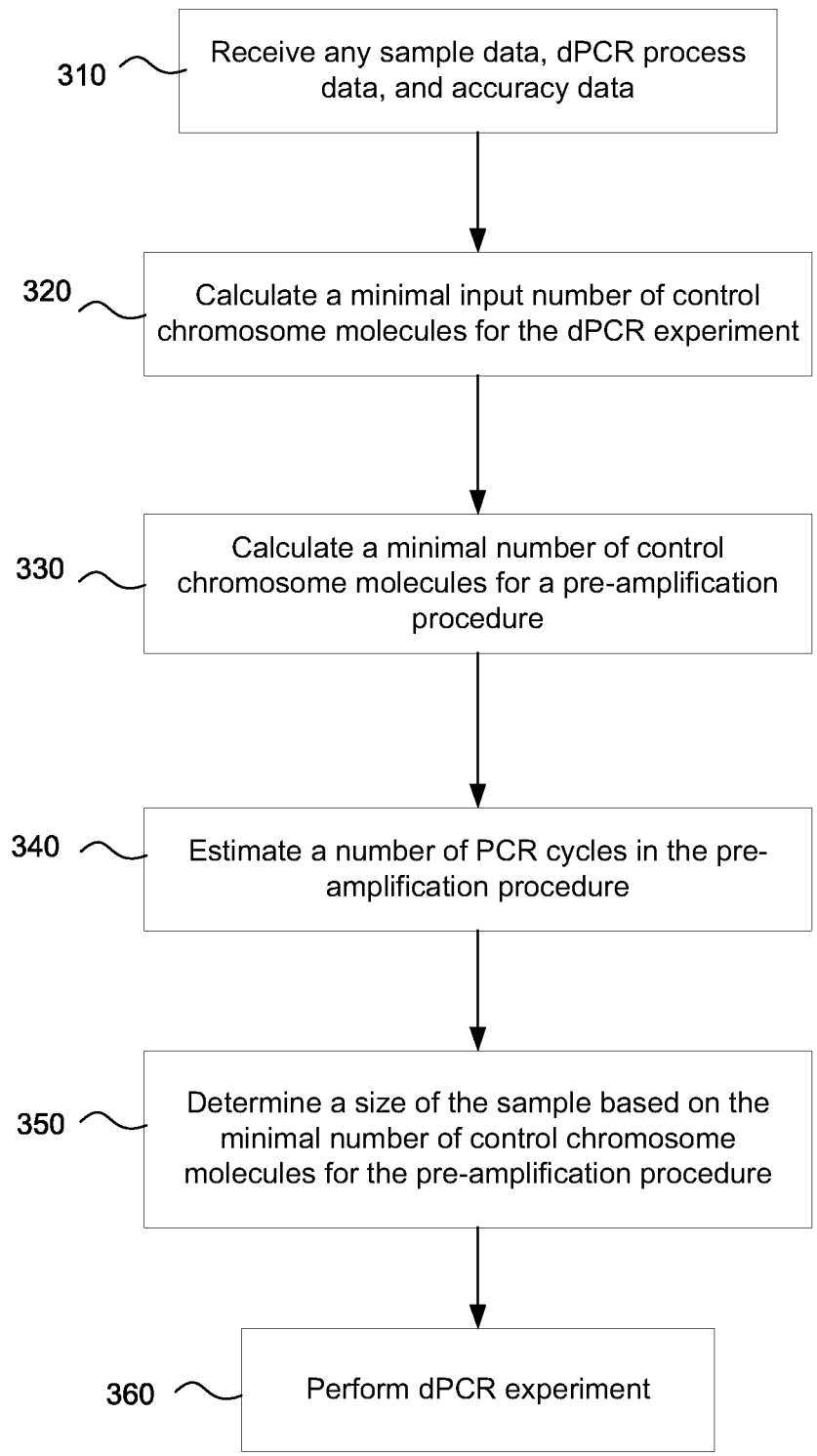
FIG. 3 is a flowchart of a method 300 of determining settings for a digital PCR (dPCR) experiment involving pre-amplification of DNA molecules in a plasma sample from a female pregnant with a fetus according to embodiments of the present invention.

FIG. 3 is a flowchart of a method 300 of determining settings for a digital PCR (dPCR) experiment involving pre-amplification of DNA molecules in a plasma sample from a female pregnant with a fetus according to embodiments of the present invention. The dPCR experiment is for the detection of a chromosomal aneuploidy. Method 300 can be performed by a computer system.

In step 310, data is received. The data can include data mentioned above. For example, the received data can include sample data, dPCR process data, and accuracy data.

In step 320, a minimal input number of control chromosome molecules for the dPCR experiment can be calculated based on at least a portion of the received data. For example, the error rate criteria, the fetal DNA fraction, data about PCR efficiencies, and the degree of aneuploidy can be used to calculate the minimal input number of control chromosome molecules. In one embodiment, minimal input number of control chromosome molecules for the dPCR experiment can be calculated using equation (29), described below. In another embodiment, minimal input number of control chromosome molecules for the dPCR experiment can be calculated using the minimal detectable relative difference in expected numbers, e.g., by identifying when the detectable relative difference in expected numbers for given error rates matches the value for the fetal DNA fraction.

Figure 4:
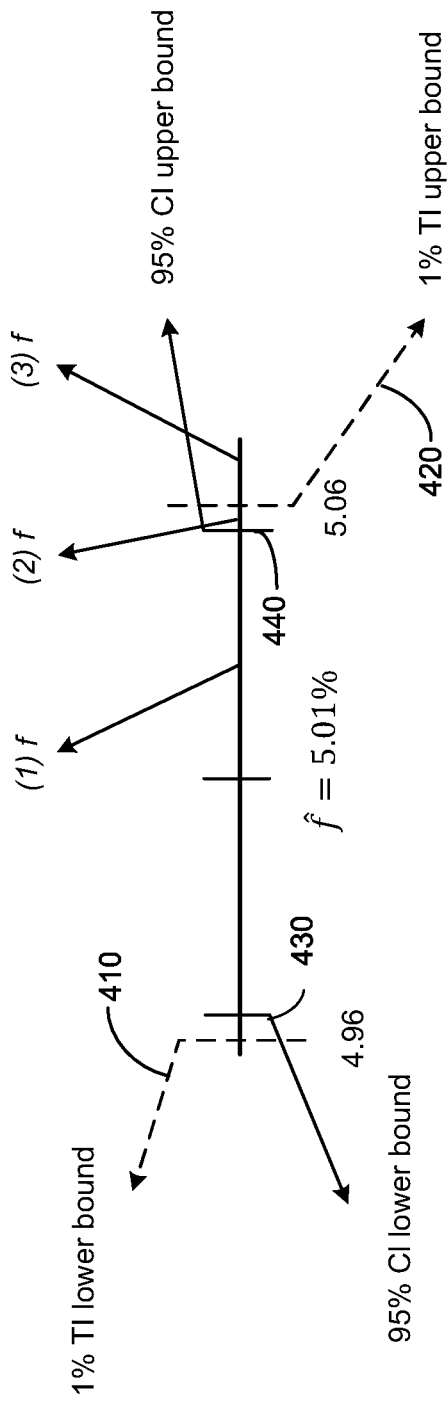
FIG. 4 shows a derivation of the input number of molecules to a pre-amplification according to embodiments of the present invention.

In step 330, a minimal number of control chromosome molecules for a pre-amplification procedure can be calculated based on at least a portion of the received data. For example, the fetal DNA fraction, the fetal DNA fraction error tolerance, and the error control number can be used. In one embodiment, equation (34) is used. FIG. 4 describes various embodiments that can be used.

In step 340, a number of PCR cycles in the pre-amplification procedure can be estimated based on at least a portion of the received data. For example, the minimal input number of control chromosome molecules for the dPCR experiment, the minimal number of control chromosome molecules for the pre-amplification procedure, the data about PCR efficiencies for the pre-amplification procedure, the number of loci for the pre-amplification, and the portion constraint can be used. In one embodiment, equation (37) is used.

In step 350, a size of the sample is determined based on the minimal number of control chromosome molecules for the pre-amplification procedure. The amount of DNA per volume can be used to determine the size of the sample. For example, based on the minimal number of molecules to the pre-application procedure, the size of a sample can be determined based on a concentration of DNA in a sample. In one embodiment, a concentration of DNA and plasma can be assumed to be about 1,500 genomic equivalents (GE) per milliliter, or about 315 GE per nanogram.

In step 360, the dPCR experiment is performed. The dPCR experiment can provide a first number of partitions that are positive for a DNA fragment from any one of a plurality of loci on the control chromosome(s) and a second number of partitions that are positive for a DNA fragment from any one of a plurality of loci on the test chromosome. The numbers can be used to determine a test metric, which can be compared to a cutoff value to provide a detection of whether a fetus has the particular chromosomal aneuploidy that is being tested.

III. REQUIRED AMOUNT OF DNA FOR DIGITAL PCR

This section describes a determination of the required amount of DNA to input to the dPCR experiment to achieve desired error rates according to various embodiments. Different error rates and potentially other inputs can impact required amount of DNA. The required amount of DNA can be quantified in various ways, e.g., by the total amount of all DNA molecules in the entire sample or by a number of control DNA molecules for control chromosome(s). Further, a relative difference in expected numbers of molecules can be calculated, which in turn can be used to determine the required amount of DNA to input to the dPCR experiment.

Here, we calculate the general formula for the relative difference in expected numbers of molecules for any degree of aneuploidy after a pre-amplification. Even though we focus on aneuploidy in chromosome 21, the formula applies to aneuploidy in any chromosome.

A. Notation

Here, we introduce some notation related to a pre-amplification procedure, and used to illustrate certain calculations.

$L_i$: number of loci for chromosome i, i=1, . . . , 23.

$y_i^l$: pre-amplification PCR efficiency per cycle for chromosome i at locus l, i=1, . . . , 23, l=1, . . . , , where chromosome 23 denotes the sex chromosomes.

$Z_{0fi}^l$: number of input chromosome i fetal molecules at locus l to a pre-amplification, i=1, . . . , 23, l=1, . . . , $L_i$.

$Z_{0mi}^l$: number of input chromosome i mother molecules at locus l to a pre-amplification, i=1, . . . , 23, l=1, . . . , $L_i$.

$Z_{pfi}^l$: number of resulted chromosome i fetal molecules at locus l from a pre-amplification with p PCR cycles in the ideal situation when $y_i^l$=100%, i=1, . . . , 23, l=1, . . . , $L_i$.

$Z_{pmi}^l$: number of resulted chromosome i mother molecules at locus l from a pre-amplification with p PCR cycles in the ideal situation when $y_i^l$=100%, i=1, . . . , 23, l=1, . . . , $L_i$.

$X_{pfi}^l$: number of resulted chromosome i fetal molecules at locus l from a pre-amplification with p PCR cycles in the real situation when $y_i^l \leq$100%, i=1, . . . , 23, l=1, . . . , $L_i$.

$X_{pmi}^l$: number of resulted chromosome i mother molecules at locus l from a pre-amplification with p PCR cycles in the real situation when $y_i^l \leq$100%, i=1, . . . , 23, l=1, . . . , $L_i$.

$Z_{pfi}$: number of resulted chromosome i fetal molecules from a pre-amplification with p PCR cycles in the ideal situation when $y_i^l$=100%, i=1, . . . , 23.

$Z_{pmi}$: number of resulted chromosome i mother molecules from a pre-amplification with p PCR cycles in the ideal situation when $y_i^l$=100%, i=1, . . . , 23.

$X_{pfi}$: number of resulted chromosome i fetal molecules from a pre-amplification with p PCR cycles in the real situation when $y_i^l \leq$100%, i=1, . . . , 23.

$X_{pmi}$: number of resulted chromosome i mother molecules from a pre-amplification with p PCR cycles in the real situation when $y_i^l \leq$100%, i=1, . . . , 23.

B. Relative Difference in Expected Numbers of Molecules

The relative difference in expected numbers of molecules quantifies on average how many more aneuploid chromosome molecules than normal chromosome molecules in a patient's plasma (containing a certain fraction of cell-free fetal DNA) are input to a dPCR experiment after a pre-amplification based on specified input variables. The relative difference can depend on various values, such as the fetal DNA fraction and the degree of aneuploidy. The discussion below focuses on chromosome 21 being the test chromosome, but the discussion applies equally to using other test chromosomes.

1. Assumptions and Pre-Amplification

Various assumptions are made for ease of explanation. These assumptions may be used in the actual calculations, or explicit values may be obtained. In one aspect, it is reasonable to assume that the input number of molecules to a pre-amplification is equal across loci on a chromosome. In an ideal amplification, the number of molecules at a locus doubles for each amplification cycle. The relationship between a starting number of fetal molecules at a locus and a resulting number fetal molecules is provided as $Z_{pfi}^l = 2^p Z_{0fi}^l$. For a real (non-ideal) amplification, the relationship is $X_{pfi}^l = (1+y_i^l)^p Z_{0fi}^l / Z_{0fi}^l$. Accordingly, the relationship between the resulting numbers for the ideal amplification and the real amplification is as follows:

$$X_{pfi}^l = \left(\frac{1+y_i^l}{2}\right)^p Z_{pfi}^l. \quad (1)$$

The same relationship holds for $X_{pmi}^l$ and $Z_{pmi}^l$.

The total number of molecules on a particular chromosome for the mother and the fetus can be determined as a sum of the values in each of the loci on the particular chromosome. The relationship between locus- and chromosomal-specific number of molecules is as follows:

$$X_{pfi} = \sum_{l=1}^{L_i}\left(\frac{1+y_i^l}{2}\right)^p Z_{pfi}^l, X_{pmi} = \sum_{l=1}^{L_i}\left(\frac{1+y_i^l}{2}\right)^p Z_{pmi}^l, \quad (2)$$

where $Z_{pfi} = L_i Z_{pfi}^l$, $Z_{pmi} = L_i Z_{pmi}^l$, $\forall l$.

For ease of notation and as a special case of our model, we can assume the same number of loci for all chromosomes such that $L_i = L$, $\forall i$. Assume all the fetal chromosomes except chromosome 21 are normal, and all the mother chromosomes are normal, we have the following relationships:

$$Z_{pfi} = \frac{L_i}{L_1} Z_{pf1}, i \neq 21. \quad (3)$$

$$Z_{pmi} = \frac{L_i}{L_1} Z_{pm1}, \forall i \quad (4)$$

When equations (3) and (4) hold, a chromosome besides chromosome 21 can be used as the control chromosome.

2. Fetal Fraction Before Pre-Amplification

This section describes determining an estimate of the fetal fraction before a pre-amplification using a portion of plasma from the whole maternal plasma. We use a separate portion of plasma from the whole maternal plasma for measuring fetal fraction than that for a pre-amplification, because the genetic marker used to measure fetal fraction may be destroyed by the pre-amplification process. We perform s cycles of PCR on this separate portion of plasma for measuring fetal fraction, and assume that fetal fraction in this PCR product is the same as that in the other portion of plasma input to the pre-amplification at the same locus containing the genetic marker. We denote $f_i(i \neq 21)$ to be the estimated fetal fraction based on chromosome i using the first approach before a pre-amplification.

Mathematically, $$f_i = \frac{V_{sfi}^1}{V_{sfi}^1 + V_{smi}^1} = \frac{U_{0fi}^1}{U_{0fi}^1 + U_{0mi}^1} = \frac{Z_{0fi}^1}{Z_{0fi}^1 + Z_{0mi}^1}, \quad (5)$$

where $(V_{sfi}^l, V_{smi}^l)$ are numbers of (fetal, maternal) molecules at the locus containing the genetic marker in the portion of plasma measuring fetal fraction after s PCR cycles, and $(U_{0fi}^l, U_{0mi}^l)$ are initial numbers of (fetal, maternal) molecules at the locus containing the genetic marker in the same portion of plasma measuring fetal fraction. The second equality of equation (5) comes from our assumption that fetal fraction in the portion of plasma for measuring fetal fraction is the same as that in the other portion of plasma input to a pre-amplification. To meet this assumption, we use the same amount of plasma for measuring fetal fraction as that for a pre-amplification.

Equations (3), (4) and (5) imply that all $f_i$'s are the same, that is, $f_i = f, 0 \leq f < 1, \forall i, i \neq 21$. Thus, $$Z_{pfi} = \frac{f}{1-f} Z_{pmi}, \forall i, i \neq 21. \quad (6)$$

In the situation of male pregnancy, the fraction of fetal molecules can also be measured using a portion of plasma ($f_i^*$) separate from that for a pre-amplification by twice of the number of chromosome Y molecules divided by the total number of chromosome i molecules, where $i \neq 21$. Mathematically, $$f_i^* = \frac{2V_{sY}^1}{V_{si}^1} = \frac{2U_{0Y}^1}{U_{0i}^1} = \frac{2Z_{0Y}^1}{Z_{0i}^1}, \forall i, i \neq 21. \quad (7)$$

As in the female fetus case, all the $f_i^*$ are equal $\forall i, i \neq 21$. We denote $f_i^* = f^*$. The discussion below uses a single notation for the fetal DNA fraction.

3. Efficiency of Pre-Amplification

The efficiency for a pre-amplification cycle can be different for each locus on each chromosome. And, the number of loci can be different for the test chromosome and the control chromosome. The discussion below accounts for different efficiencies at different loci. The efficiencies are averaged to obtain the real number of molecules on a chromosome. The relationship between the starting number of fetal/maternal molecules and ending number of fetal/maternal molecules is provided in equation (8), which effectively averages the efficiencies across the loci of a given chromosome and then multiplies that value by the ideal number of molecules on the chromosome, after the pre-amplification procedure.

Let c be the index for the control chromosome. We have the following relationships $$X_{pf21} = \frac{1}{L_{21}} \sum_{l=1}^{L_{21}} \left( \frac{1 + y_{21}^l}{2} \right)^p Z_{pf21}, X_{pmc} = \frac{1}{L_c} \sum_{l=1}^{L_c} \left( \frac{1 + y_c^l}{2} \right)^p Z_{pmc}. \quad (8)$$

$L_{21}$ is the number of loci on chromosome 21. $L_c$ is a number of loci on the control chromosome. The efficiency for each locus can be measured as described in references [9] and [10].

4. Degree of Aneuploidy

The degree of aneuploidy h corresponds to the type of aneuploidy being tested. The degree of aneuploidy is greater than one for trisomy, as less than one for monosomy. An aneuploidy greater than trisomy has a degree of aneuploidy higher than that of trisomy. The degree of aneuploidy will impact the position of expectation value Δ 125 in FIG. 1, as a higher degree of aneuploidy will cause a larger expectation value Δ 125.

In one embodiment, the degree of aneuploidy h is defined to be the ratio of input number of fetal chromosome 21 molecules to that of fetal control chromosome at a locus l $$h = \frac{Z_{0f21}^l}{Z_{0fc}^l} = \frac{Z_{pf21}^l/2^p}{Z_{pfc}^l/2^p} = \frac{Z_{pf21}/L_{21} 2^p}{Z_{pfc}/L_c 2^p} = \frac{L_c Z_{pf21}}{L_{21} Z_{pfc}}. \quad (9)$$

In other words, h=1.5 for trisomy, h=1 for normal, and h=0.5 for monosomy.

5. Relationship between Maternal Control and Fetal Test

Once the degree of aneuploidy is defined, a relationship can be defined between the number of molecules for the test chromosome and a number of molecules for the control chromosome after an ideal pre-amplification. The following equation holds $$Z_{pf21} = h \frac{L_{21}}{L_c} Z_{pfc} = \frac{hf}{1-f} \frac{L_{21}}{L_c} Z_{pmc}, \quad (10)$$

The first part shows the relationship between the ending number fetal molecules of chromosome 21 relative to the ending number of fetal molecules of the control chromosome, with a number of loci of each chromosome can differ. The second part shows the relationship between the ending number of maternal molecules of the control chromosome and the ending number of fetal molecules on a control chromosome, which is dependent on the fetal DNA fraction $f$. This second part is defined by the relationship $$Z_{pfc} = \frac{f}{1-f} Z_{pmc}.$$

The relationship between the number of maternal molecules of the control chromosome and a number of fetal molecules on the test chromosome after a non-ideal pre-amplification can be determined as follows. By equation (8), we have $$X_{pf21} = \frac{1}{R} \frac{hf}{1-f} X_{pmc}, \text{ where} \quad (11)$$

$$R = \frac{\sum_{l=1}^{L_c} \left( \frac{1 + y_c^l}{2} \right)^p}{\sum_{l=1}^{L_{21}} \left( \frac{1 + y_{21}^l}{2} \right)^p}. \quad (12)$$

6. Input to a dPCR Experiment

In some embodiments, only a fraction of molecules resulting from a pre-amplification procedure is input to a dPCR experiment, e.g., due to instrument-specific constraint in input DNA volume and need to dilute output of pre-amplification procedure. The dPCR experiment has a certain number of partitions, each of which can accommodate up to a maximum amount of volume. Thus, there is a volume restriction, which becomes more acute when the pre-amplification output needs to be diluted, e.g., to dilute out reagents (e.g., primers) from pre-amplification procedure. As an example, around or at least a 10-fold dilution can be performed.

Herein, the fraction τ corresponds to the fraction of molecules resulting from a pre-amplification procedure that is input to the dPCR experiment. The value of τ can be selected prior to calculations described herein. An example value of τ is 0.005. Accordingly, τ is a portion constraint that specifies a portion of DNA molecules resulting from a pre-amplification procedure to be input to the dPCR experiment.

Multiplying both sides of equation (11) by τ and taking expectation on both sides, equation (13) provides the expression for the expected number of fetal chromosome 21 molecules input to a dPCR experiment.

$$\mu_{pf21} = \frac{1}{R} \frac{hf}{1-f} \mu_{pmc}. \quad (13)$$

Since for the mother, $$Z_{pmc} = \frac{L_c}{L_{21}} Z_{pm21},$$

equation (8) implies $X_{pmc} = R X_{pm21}$ which further implies $$\mu_{pmc} = R\mu_{pm21}. \quad (14)$$

Therefore, the expected number of fetal chromosome 21 molecules input to a dPCR experiment becomes $$\mu_{pf21} = \frac{hf}{1-f} \mu_{pm21}. \quad (15)$$

Similarly, the expected number of fetal control chromosome molecules input to a dPCR experiment is $$\mu_{pfc} = \frac{Rf}{1-f} \mu_{pm21}. \quad (16)$$

Equations (15) and (16) lead to expected numbers of chromosome 21 ($\mu_{p21}$) and control chromosome ($\mu_{pc}$) molecules input to a dPCR experiment, respectively:

$$\mu_{p21} = \mu_{p21} + \mu_{pm21} = \left(\frac{hf}{1-f} + 1\right)\mu_{pm21} \quad (17)$$

$$\mu_{pc} = \mu_{pfc} + \mu_{pmc} = \left(\frac{f}{1-f} + 1\right)R\mu_{pm21}. \quad (18)$$

7. Relative Difference in Expected Numbers of Molecules

We define $\Delta\mu_p = \mu_{p21} - \mu_{pc}$, the difference between expected numbers of chromosome 21 and control chromosome molecules input to a dPCR experiment. Thus, the relative difference in expected numbers of molecules is $$\frac{\Delta u_p}{\mu_{pc}} = \frac{1}{R}(hf + 1 - f) - 1. \quad (19)$$

In the case of male pregnancy, fraction of fetal DNA $f^*$ could be measured instead of $f$. We can show that $f^* = f$. Therefore, we can simply replace $f$ by $f^*$ when fetus is male. Equation (19) becomes $$\frac{\Delta u_p}{\mu_{pc}} = \frac{1}{R}(hf^* + 1 - f^*) - 1. \quad (20)$$

Based on equations (19) and (20) while dropping the R factor for ease of illustration we have the ratio $$\frac{\mu_{p21}}{\mu_{pc}}$$

to be 1.3, 1.25, 1.2, and 1.15 for fetal fractions 60%, 50%, 40%, and 30% when there is chromosome 21 trisomy. The relative difference in equation (19) can help to define the minimal detectable relative difference, as described below.

C. Minimal Number of Control Chromosome Molecules Input to a dPCR Experiment

In this section, a statistical hypothesis testing framework is used to estimate the minimal number of control chromosome molecules required for a dPCR experiment and minimal detectable relative difference in expected numbers of molecules when controlling false positive and false negative rates at certain levels. The data from a dPCR experiment contain signal intensities for two or more different channels (at least one measures the intensities of the chromosome being tested from all partitions, and at least one measures control chromosome intensities). In dPCR, the magnitude of the intensity in a partition does not determine the number of molecules in that partition. The signal only conveys whether or not a partition contains any molecule type (i.e., corresponding to a particular channel, which may be a particular locus). Therefore, data available for follow-up analyses are binary: positive or negative partitions for each molecule type.

Herein, $W_{p21}$ and $W_{pc}$ denote the estimated numbers of chromosome 21 and control chromosome molecules calculated from observed proportions of positive partitions. These numbers can be calculated, as described above. For example, in a single-volume experiment, the number of molecules can be determined using a Poisson distribution with means $\mu_{p32}/N$ and $\mu_{pc}/N$, respectively, where N is the number of partitions. Other embodiments can use the number of positive partitions as the number of molecules.

The expected numbers of chromosome 21 and control chromosome molecules input to a dPCR experiment ($\mu_{p21}$ and $\mu_{pc}$) can be compared to determine a classification of the sample, e.g., normal or aneuploidy. As examples, the two expected numbers can be compared to each other by a taking a difference, a ratio of the two values, or a combination of such functions, or differences or ratios of functions that have these expected values as inputs. The null and alternative hypotheses equivalent to $H_0$:h=1 (normal) and $H_1$:h>1 (e.g., trisomy, tetrasomy, or pentasomy) are $$H_0: \frac{\mu_{p21}}{\mu_{pc}} = g(1) \quad (21)$$

$$H_1: \frac{\mu_{p21}}{\mu_{pc}} = g(h), h > 1. \quad (22)$$

For the following discussion, we focus on aneuploidy of extra copie(s) of the test chromosome. Similar arguments can apply to monosomy with the alternative hypothesis replaced by $H_1$:h=0.5. Given fixed values of $f$, $y_{21}^l$, and $y_c^l$, the function g(h) is a monotonic increasing function in h such that $\mu_{p21} = g(h)\mu_{pc}$, and is defined by equation (19) as $$g(h) = \frac{1}{R}(hf + 1 - f). \quad (23)$$

Although a ratio or difference of the number of molecules from each chromosome (e.g., $W_{p21}/W_{pc}$, $W_{p21}-W_{pc}$, and $W_{p21}/(W_{pc}+W_{p21})$) can be used as test statistic, other test statistics may be used. For example, test statistics W1-W4 in reference [6] can be used. To compare two Poisson rates, a variance stabilizing transformation test statistic that is simple, conservative, and of high power is used. Since control of false negative rate can be more crucial than false positive rate in non-invasive prenatal testing, the following test statistic is sued in order to reach higher power (lower false negative rate) than other test statistics. The test statistic is $$J(W_{p21}, W_{pc}) = \frac{2\left(\sqrt{W_{p21} + \frac{3}{8}} - \sqrt{\rho\left(W_{pc} + \frac{3}{8}\right)}\right)}{\sqrt{1+\rho}}, \qquad (24)$$

where $\rho = g(1) = 1/R$. By [5] and [6], $J(W_{p21}, W_{pc})$ follows the standard Normal distribution.

For the rest of this description, we simply denote $(W_{p21}, W_{pc})$ by J. In order to control false positive rate to be less than or equal to $\alpha$, we need the following relationship to hold:

$$P(J > z_{1-\alpha} | H_0) \leq \alpha. \qquad (25)$$

In order to control false negative rate at $\beta$, we need the following relationship to hold:

$$P(J > z_{1-\alpha} | H_1) \geq 1-\beta. \qquad (26)$$

As shown in reference [6], for equations (25) and (26) to hold, the function $v(h, \mu_{pc})$ has to be greater than or equal to 0, where $$v(h, \mu_{pc}) = \qquad (27)$$
$$2\left(\sqrt{g(h)} - \sqrt{g(1)}\right)\sqrt{\mu_{pc} + \frac{3}{8}} - z_{1-\beta}\sqrt{1+g(h)} - z_{1-\alpha}\sqrt{1+g(1)},$$

where $z_{1-\alpha}$ and $z_{1-\beta}$ are the $100(1-\alpha)$% th and $100(1-\beta)$% th quantiles of the standard Normal distribution, respectively. In the case of a monosomy, the function $v(h,\mu_{pc})$ has to be less than or equal to 0. As a reminder, more molecules will move the expectation value for the alternative hypothesis further from that of the null hypothesis, thereby allowing a lower false negative rate. For equation (27) to be $\geq 0$, the more stringent the error rates, the larger $z_{1-\beta}$ and $z_{1-\alpha}$ are, and the larger $\mu_{pc}$ has to be. In other words, one has to input more molecules in order to reach the desired error rates. Other equations will result when different test metrics are used.

This relationship is useful for experimental design purpose. For a given $\mu_{pc}$, one can use $v(h,\mu_{pc})$ to determine the minimal detectable relative difference in expected numbers of molecules controlling false positive and false negative rates at certain levels. The minimal detectable relative difference in expected numbers of molecules can be calculated from equation (27) by fixing $\mu_{pc}$ to a specific value and finding the smallest h, such that $h > 1$ and $v(h,\mu_{pc}) \geq 0$.

Second, given a h, $h > 1$ (e.g. h=1.5 in $T_{21}$ case), one can use the below inequality to determine the required input number of control chromosome molecules to a dPCR experiment in order to detect an aneuploidy at certain levels of false positive and false negative rates by assuming $$R = \frac{L_c}{L_{21}}$$

$$\mu_{pc} \geq \hat{\mu}_{pc} \qquad (28)$$

where $$\hat{\mu}_{pc} = \left(\frac{z_{1-\beta}\sqrt{1+g(h)} + z_{1-\alpha}\sqrt{1+g(1)}}{2\left(\sqrt{g(h)} - \sqrt{g(1)}\right)}\right)^2 - \frac{3}{8}. \qquad (29)$$

In the case of a monosomy, equation (29) also holds with h replaced by 0.5.

Equation (29) provides the minimal number of DNA molecules from the control chromosome (also referred to as control molecules) to be input to the dPCR experiment that will provide the desired error criteria. The minimal number of control molecules can be obtained in a variety of ways, e.g., having a larger number of control molecules to input to the pre-amplification procedure, using more loci on the chromosomes, and performing more cycles in the pre-amplification procedure. In one implementation, the minimal detectable relative difference in numbers of molecules can be calculated from equation (27) by fixing $\mu_{pc}$ to a specific value and finding the smallest h, such that $h > 1$ and $v(h,\mu_{pc}) \geq 0$ Accordingly, in one embodiment, the minimal number of DNA molecules from the control chromosome can be determined using the error criteria $\alpha$ and $\beta$, the degree of aneuploidy h, data about the pre-amplification efficiencies (e.g., as signified by R or a lower bound for the efficiencies, or simply an assumption of equal average efficiencies, and thus $$R = \frac{L_c}{L_{21}}),$$

and the fetal DNA fraction $f$.

The smaller the error rates, the larger the values for $z_{1-\alpha}$ and $z_{1-\beta}$, and thus the more input molecules are needed, since lower error rates require more molecules to separate the distributions. The larger the value of g(h), $h > 1$, the fewer number of molecules are needed. The larger the fetal DNA fraction, the larger the separation between the two distributions. And, a higher aneuploidy will all increase the separation between the two distributions.

IV. MINIMAL NUMBER OF CONTROL CHROMOSOME MOLECULES INPUT TO A PRE-AMPLIFICATION

To control the standard error of fetal fraction in a sampled plasma input to a pre-amplification, embodiments can control the relative error defined in equation (30) between unknown expected fetal fraction ($f_0$) in the whole plasma and the fetal fraction ($f$) from the sampled plasma to be less than or equal to $\psi$.

$$\frac{|f_0 - f|}{f} \leq \psi. \qquad (30)$$

Equation (30) is equivalent to the below equation $$f - \psi f \leq f_0 \leq f + \psi f. \quad (31)$$

$\psi$ is the fetal DNA fraction error tolerance. Thus, $\psi$ specifies how close the fetal DNA fraction is in the sampled plasma to the actual fetal fraction. An example value of $\psi$ is 1% (i.e., 0.01), which corresponds to $\leq 1\%$ relative error of the fetal DNA fraction in the sample plasma to the actual fetal DNA fraction. The smaller $\psi$ is, the more accurate the fetal fraction in the sampled plasma.

To control the probability that a relative error is less than or equal to $\psi$ is at least $100(1-\eta)\%$, embodiment can require that the width of the $100(1-f)\%$ confidence interval (CI) for the expected fetal fraction is shorter than $2\psi$ from $f$.

$$z_{1-\frac{\eta}{2}} \sqrt{\frac{f(1-f)}{Z_{0c}}} \leq \psi f, \quad (32)$$

where $$z_{1-\frac{\eta}{2}}$$

is the $$100\left(1 - \frac{\eta}{2}\right)\% \ th$$

quantile of the standard Normal distribution. An example value of $\eta$ is 5%, thereby providing 95% probability that fetal fraction in the sampled plasma is within tolerance. Accordingly, $\eta$ is an error control number that controls a probability that a relative error between an unknown expected fetal DNA fraction and a fetal DNA fraction from the plasma to be within the fetal DNA fraction error tolerance $\psi$.

Therefore, the required total number of control chromosome molecules input to a pre-amplification must satisfy the below inequality $$Z_{0c} \geq \hat{Z}_{0c}, \text{ where} \quad (33)$$

$$\hat{Z}_{0c} = \frac{z_{1-\frac{\eta}{2}}^2}{\psi^2}\left(\frac{1}{f} - 1\right). \quad (34)$$

Equation (34) provides the minimal number of control chromosome molecules for the pre-amplification procedure. Accordingly, in one embodiment, the minimal number of control chromosome molecules for the pre-amplification procedure can be determined based on the fetal DNA fraction $f$, the fetal DNA fraction error tolerance $\psi$, and the error control number $\eta$, where fetal fraction $f$ is measured using a separate portion of plasma from the whole plasmaBy using the same amount of plasma for measuring fetal fraction as that for pre-amplification, we ensure that the accuracy of the measured fetal fraction is within a reasonable range.

The higher the probability $100(1-\eta)\%$ is, the higher the minimal number is, since it takes more molecules to reach the higher probability of being within the error tolerance. And, the smaller the error tolerance, the larger the minimal number, as there is more variation with a smaller number of molecules. And, the smaller the fetal DNA fraction, the more molecules are needed, since it takes more molecules to get enough fetal DNA molecules to reach a more accurate fetal DNA fraction.

FIG. 4 shows a derivation of the input number of molecules to a pre-amplification according to embodiments of the present invention. By showing that if we choose the interval of equation (31) in a way such that it covers the $(100-\eta)\%$ confidence interval for the unknown expected fetal fraction in the whole plasma, the probability that this interval contains the unknown expected fetal fraction in the whole plasma is at least $(100-\eta)\%$. To see this, suppose the fetal fraction in the sampled plasma for a pre-amplification is 5.01%. By setting $\psi$ to be 1% in equation (31), the corresponding interval is [4.96, 5.06] (red dashed vertical lines 410 and 420).

Suppose the two solid black vertical lines 430 and 440 in the FIG. 4 are the upper- and lower-bounds for the 95% CI. By placing the red dashed vertical lines 410 and 420 such that the interval they form covers that formed by the two solid black vertical lines 430 and 440, there are three possibilities where the expected fetal fraction can fall: locations (1), (2), and (3). If the expected fetal fraction falls at (1), both 95% CI and the interval from equation (31) cover it. If the expected fetal fraction falls at (2), only the interval from equation (31) covers it. If the expected fetal fraction falls at (3), neither of the intervals covers it. Thus, the probability that the interval from equation (31) covers the expected fetal fraction is at least 95%. Finally, the requirement that the interval from equation (31) covers the $(100-\eta)\%$ CI leads to equation (32).

In other embodiments, if there is a large number of loci and a dPCR instrument with big enough volume, it is possible to skip the pre-amplification step.

V. CALCULATING PCR CYCLES

Thus, based on equations (29) and (34), embodiments can calculate the number of PCR cycles required for a pre-amplification using the below inequality:

$$\sum_{l=1}^{L_C}(1 + y_c^l)^p \geq \frac{\hat{\mu}_{pc}}{\tau \hat{Z}_{0c}}. \quad (35)$$

Practically, equation (35) can be solved using the below closed-form formula by assigning a lower bound $y_0$ for PCR efficiency, and thus $y_c^l = y_0, \forall l$.

$$p \geq \hat{p}, \text{ where} \quad (36)$$

$$\hat{p} = \log_{(1+y_0)}\frac{\hat{\mu}_{pc}}{\tau \hat{Z}_{0c} L_c}. \quad (37)$$

Equation (35) can be derived from the requirement that the input number of pre-amplification molecules multiplied by the average efficiency rate (sum divided by number of loci) for the control chromosome provides the number of output control molecules, which is reduced by the portion constraint $\tau$ should be more than the minimal input required for the dPCR experiment.

Accordingly, the number of PCR cycles in the pre-amplification procedure can be determined based on the minimal input number of control chromosome molecules for the dPCR experiment, the minimal input number of control chromosome molecules for the pre-amplification procedure, the lower bound for PCR efficiencies for the pre-amplification procedure, the number of loci for the pre-amplification, and the portion constraint.

VI. RESULTS

All the results described in this section assume all the PCR efficiencies equal to 0.95, fetal fraction relative error tolerance $\psi$=0.05, fetal fraction error control number $\eta$=0.05, and portion of a pre-amplification volume input to a dPCR experiment is $\tau$=0.005. We assume equal numbers of loci for the test and control chromosomes, and try 3 different numbers of loci (1, 12, and 96 loci) to see how the number of loci affects the required number of PCR cycles. Given certain false positive and false negative rates, we first estimate the required input number of control chromosome molecules to a dPCR experiment using equation (29). Given a fetal fraction, we estimate the required input number of control chromosome molecules to a pre-amplification using equation (34). Then, we get an estimate for the required number of PCR cycles for the pre-amplification based on these 2 numbers. We use this minimal required number of PCR cycles to calculate and plot the minimal detectable relative difference in expected numbers of molecules. The minimal detectable relative difference is helpful because one knows the range of DNA concentration in clinical samples, which defines input molecules into dPCR (without pre-amplification); or, if one does a pre-amplification one can control how much is input into dPCR based on how many cycles of pre-amplification and initial input.

Figure 5:
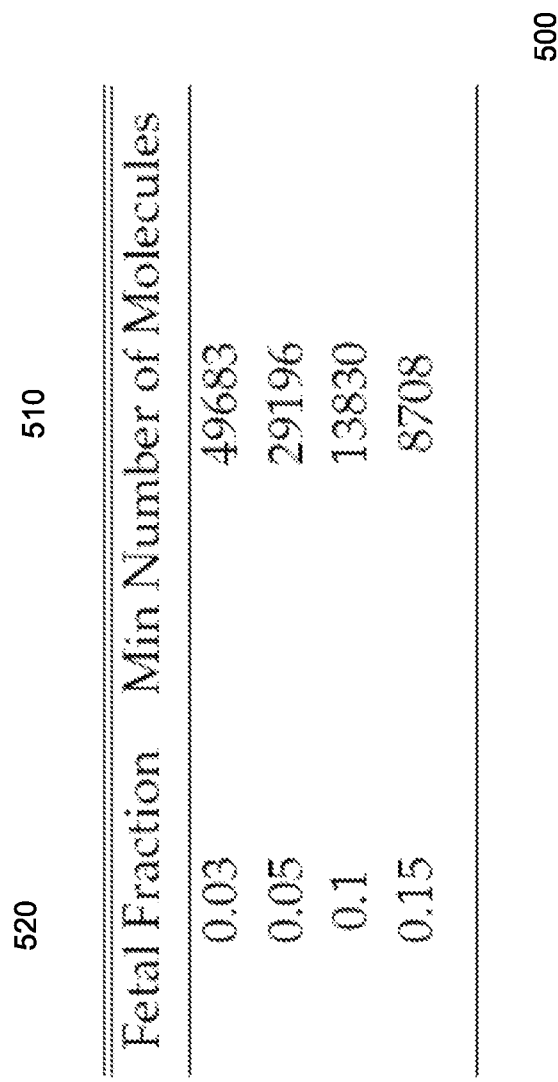
FIG. 5 is a table showing minimal input number of control chromosome molecules to a pre-amplification procedure at different fetal fractions according to embodiments of the present invention.

FIG. 5 is a table 500 showing minimal input number of control chromosome molecules 410 to a pre-amplification procedure at different fetal fractions 520 according to embodiments of the present invention. Table 500 provides minimal input number of control chromosome molecules 510 consistent with controlling the probability that a relative error between unknown expected fetal fraction in the whole plasma and the estimated fetal fraction from the sampled plasma less than or equal to 5% (fetal DNA fraction error tolerance) to be at least 95% (specified by error control number) according to embodiments of the present invention. The minimal numbers in table 500 are determined using equation (34).

FIG. 6 is a table 600 showing the minimal total number of control chromosome molecules 610-640 required to input to a dPCR experiment in order to detect $T_{21}$ under different scenarios of FP (650), FN (660) rates, and fetal fraction according to embodiments of the present invention. The minimal total number of control chromosome molecules 610-640 are calculated based on equation (29) when h=1.5. As shown, it is possible to detect a trisomy at 1% FP and 1% FN rates at a fetal fraction as low as 3%, if one inputs at least 49,683 control chromosome molecules into a pre-amplification and at least 194,590 control chromosome molecules into the dPCR experiment.

As expected, for fixed values of FP and FN rates, the higher the fetal fraction, the smaller the required total number of molecules for a dPCR experiment. For fixed values of fetal fraction, the more stringent the FP and FN rates, the more the required total number of molecules for a dPCR experiment.

FIG. 7 is a table 700 listing the minimal number of PCR cycles 710-740 required for the pre-amplification under different scenarios according to embodiments of the present invention. The various scenarios include number of loci, FP 750, FN 760 rates, and fetal fraction in order to achieve the required input number of control chromosome molecules to a dPCR experiment (table 600) from the required total input number of control chromosome molecules to the pre-amplification (Table 500). The number of cycles in table 700 are determined using equation (37).

For the example of 1% FP and 1% FN rates at a fetal fraction as low as 3% and only 1 locus, this requires at least 10 PCR cycles in the pre-amplification of 49,683 control chromosome molecules to obtain 194,590 control chromosome molecules into the dPCR experiment (i.e., given a portion constraint for the fraction 0.005 of pre-amplification output molecules to be input to the dPCR experiment). In this case, when the number of loci increases to 12, the required number of PCR cycles goes down to 7. In the same case, when the number of loci increases to a much bigger value 96, the required number of PCR cycles further goes down to 4.

Different dPCR instruments have different volumes, so the volume constraints differ across platforms. Here we did the calculations with the assumption that volume constraint is 0.005. A platform with a larger volume constraint will further reduce the PCR cycle numbers. Therefore, with a large number of loci (e.g. 96) and a dPCR platform with larger volume, it is possible to skip the pre-amplification step, which will help to reduce experimental noises. However, designing a large number of assays could be very difficult due to primer-dimer issues. If the desired number of loci could not be achieved, the pre-amplification step is still necessary.

Figure 8A:
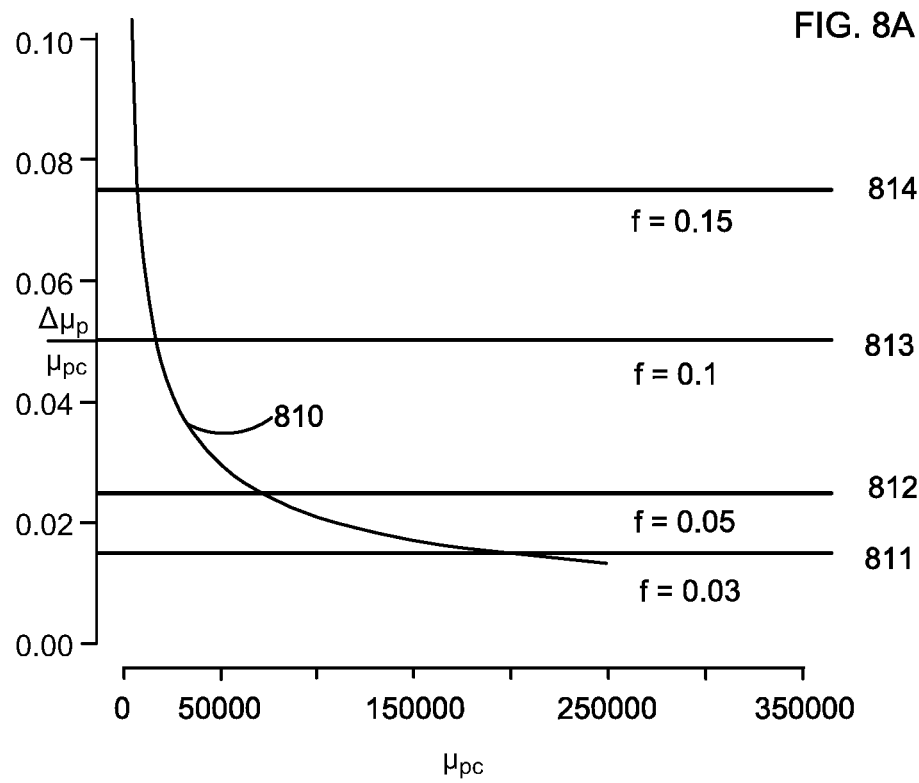
Figure 8B:
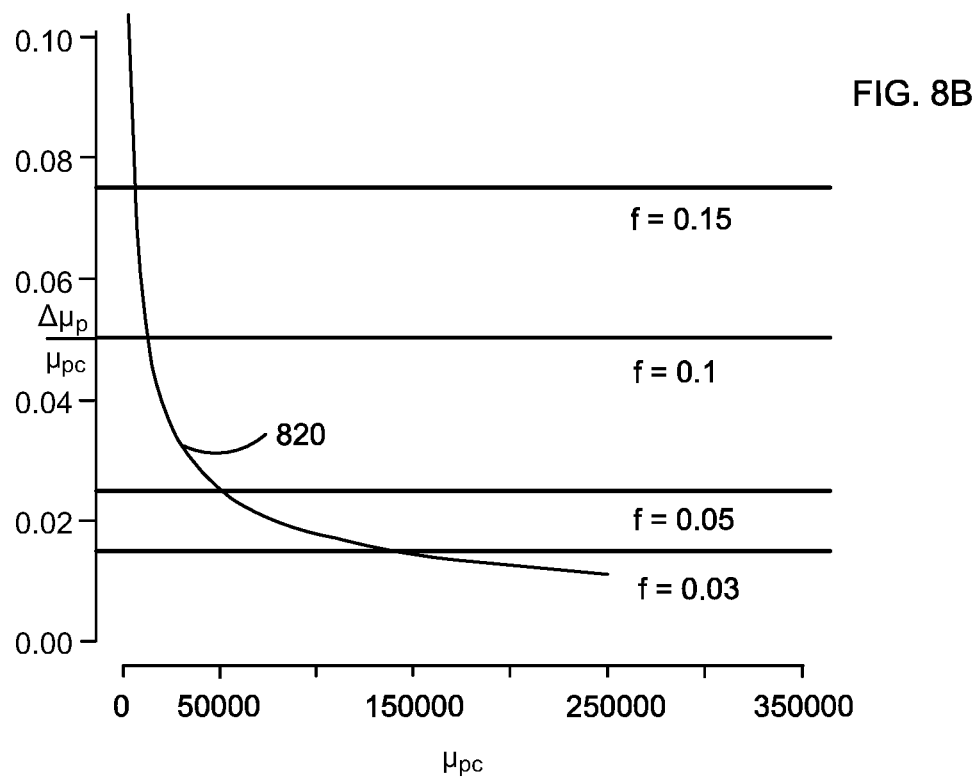

FIGS. 8A-8C show plots illustrating the relationship between minimal detectable relative difference in expected numbers of molecules (black solid line) and expected total number of control chromosome molecules $\mu_{pc}$ for different levels of FP and FN rates according to embodiments of the present invention. In FIG. 8A, the minimal detectable relative difference 810 (e.g., as determined by equation (27)) decreases as $\mu_{pc}$ increases, since more molecules allows for a smaller difference (e.g., due to low fetal DNA fraction) to be detected. The lines 811-814 (determined by equation (19)) denote different fetal DNA fractions, 3%, 5%, 10%, and 15%, respectively. The $\mu_{pc}$ at which the minimal detectable relative difference 810 and blue solid line 813 cross is the minimal required $\mu_{ps}$ for detecting $T_{21}$ when the fetal fraction is 10%.

Thus, an analysis like FIG. 8A can also be used to determine the minimal required number of molecules (i.e., instead of equations 27-29). FIG. 8A-8C show how $\mu_{ps}$ and error rates affect minimal detectable relative difference. FIG. 6 also shows that by increasing error rates, one can reduce the minimal required number of molecules. FIG. 6 can also be used for determining whether or not there is a need for a pre-amplification. Suppose one knows the range of input DNA of clinical samples is lower than the minimal required number of molecules (i.e. the range is lower than the $\mu_{pc}$ where the black and color lines crosses), then we know we need a pre-amplification in order to detect an aneuploidy at certain error rates. By contrast, if the range is higher than the minimal required number of molecules, then a pre-amplification can be skipped.

FIG. 8A corresponds to a false positive rate and false negative rate of 1%. FIG. 8B corresponds to a false positive rate and false negative rate of 2.5%. FIG. 8C corresponds to a false positive rate of 5% and false negative rate of 1%, which is an example where the two rates are different. As one can see, the minimal detectable relative difference 820 in FIG. 8B crosses the 5% fetal DNA fraction before minimal detectable relative difference 810 in FIG. 8A, which is expected since FIG. 8A has more stringent error rates. The minimal detectable relative difference 830 in FIG. 8C crosses the 5% fetal DNA fraction at about the same number of control molecules as in FIG. 8B. This is a result of a higher false positive rate, but a lower false negative rate.

In summary, embodiments provide a statistical framework for designing a dPCR experiment for non-invasive prenatal testing. Specifically, embodiments can provide a tool for determining the minimal detectable relative difference in expected numbers of molecules of a test chromosome and a control one, and minimal total number of control chromosome molecules required to input to a dPCR experiment in order to detect an aneuploidy at certain levels of false positive and false negative rates, minimal total number of control chromosome molecules required to input to a pre-amplification in order to control the relative error of fetal fraction in the sampled plasma at a certain level, and minimal number of PCR cycles required for the pre-amplification. We show that it is possible to detect a trisomy at 1% FP and 1% FN rates for a fetal fraction as low as 3%.

In some embodiments, a computer system can calculate the relative difference in expected numbers of molecules incorporating PCR efficiencies, number of PCR cycles, and fetal fraction, and use this relative difference to perform a statistical hypothesis testing for whether or not the patient being tested has an aneuploid fetus. This also leads to the minimal detectable relative difference and minimal total number of control chromosome molecules required for a dPCR experiment. We also consider different ways for measuring fetal fraction before a pre-amplification.

Example advantages of various embodiments the present invention include the following. One is the calculation of the relative difference in expected numbers of molecules under an experimental workflow with a pre-amplification step (e.g., relative difference incorporates PCR efficiencies, number of PCR cycles, degree of aneuploidy, and fetal fraction). We show that a pre-amplification step is necessary in this application due to limited amounts of cell-free fetal DNA. A second is the detection of an aneuploidy does not depend on the number of partitions, but on the total number of input molecules. Therefore, embodiments may be applied to technologies other than dPCR instruments, as long as the DNA molecules can be counted with sufficient precision (e.g. NGS technologies). A third is the test statistic comparing two Poisson rates ($\mu_{pc}$ and $\mu_{p21}$) is more powerful than other existing approaches as suggested by references [5], [8], and [6]. A fourth is the use of additional quantities of interest specific to the experimental workflow: minimal detectable relative difference in expected numbers of molecules, minimal total numbers of control chromosome molecules required for a pre-amplification and for a dPCR experiment, and minimal number of PCR cycles required for the pre-amplification. In summary, embodiments provide important quantities for use when planning a dPCR experiment for non-invasive prenatal testing.

VII. COMPUTER SYSTEM

Figure 9:
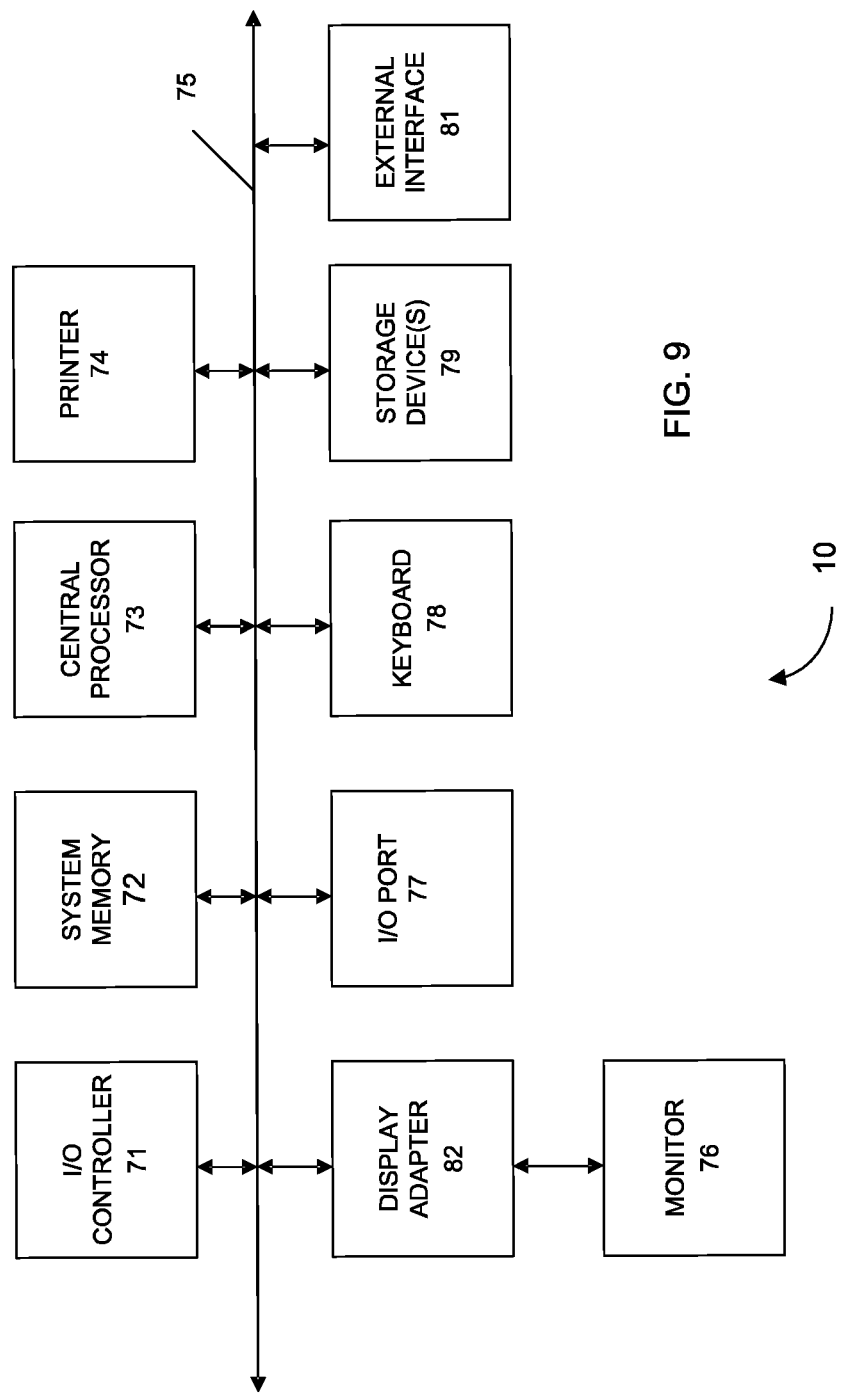
FIG. 9 shows a block diagram of an example computer system 10 usable with system and methods according to embodiments of the present invention.

Any of the computer systems mentioned herein may utilize any suitable number of subsystems. Examples of such subsystems are shown in FIG. 9 in computer apparatus 10. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 9 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire) For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, R, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned here are incorporated by reference in their entirety for all purposes. None is admitted to be prior art.

VIII. REFERENCES

1. H. Christina Fan and Stephen R. Quake. Detection of aneuploidy with digital polymerase chain reaction. Analytical Chemistry, 79(19):7576-7579, 2007.
2. Y. M. Dennis Lo, Fiona M. F. Lun, K. C. Allen Chan, Nancy B. Y. Tsui, Ka C. Chong, Tze K. Lau, Tak Y. Leung, Benny C. Y. Zee, Charles R. Cantor, and Rossa W. K. Chiu. Digital per for the molecular detection of fetal chromosomal aneuploidy. Proceedings of the National Academy of Sciences, 104(32):13116-13121, 2007.
3. Fiona M. F. Lun, Nancy B. Y. Tsui, K. C. Allen Chan, Tak Y. Leung, Tze K. Lau, Pimlak Charoenkwan, Katherine C. K. Chow, Wyatt Y. W. Lo, Chanane Wanapirak, Torpong Sanguansermsri, Charles R. Cantor, Rossa W. K. Chiu, and Y. M. Dennis Lo. Noninvasive prenatal diagnosis of monogenic diseases by digital size selection and relative mutation dosage on DNA in maternal plasma. Proceedings of the National Academy of Sciences, 105(50): 19920-19925, 2008.
4. Bernhard G. Zimmermann, Simon Grill, Wolfgang Holzgreve, Xiao Yan Zhong, Laird G. Jackson, and Sinuhe Hahn. Digital per: a powerful new tool for non-invasive prenatal diagnosis? Prenatal Diagnosis, 28(12): 1087-1093, 2008.
5. Michael D. Huffman. An improved approximate two-sample poisson test. Journal of the Royal Statistical Society. Series C (Applied Statistics), 33:224-226, 1984.
6. Kangxia Gu, Hon Keung Tony Ng, Man Lai Tang, and William R. Schucany. Testing the ratio of two poisson rates. Biometrical Journal, 50:283-298, 2008.
7. Kevin A Heyries, Carolina Tropini, Michael Vanlnsberghe, Callum Doolin, Oleh I Petriv, Anupam Singhal, Kaston Leung, Curtis B Hughesman, and Carl L Hansen. Megapixel digital per. Nat Meth, 8:649-651, 2011.
8. Hon Keung Tony Ng and Man-Lai Tang. Testing the equality of two poisson means using the rate ratio. Statistics in Medicine, 24:955-965, 2005.
9. Izaskun Mallona, Julia Weiss, and Marcos Egea-Cortines. "perEfficiency: a Web tool for PCR amplification efficiency prediction," BMC Bioinformatics 2011, 12:404.
10. Jan M. Ruijter, Michael W. Pfaffl, Sheng Zhao, Andrej Spiess, Gregory Boggy, Jochen Blom, Robert G. Rutledge, Davide Sisti, Antoon Lievens, Katleen De Preter, Stefaan Derveaux, Jan Hellemans, and Jo Vandesompele, "Evaluation of qPCR curve analysis methods for reliable biomarker discovery: Bias, resolution, precision, and implications," Methods 59 (2013) 32-46.
11. Jason E. Kreutz, Todd Munson, Toan Huynh, Feng Shen, Wenbin Du, and Rustem F. Ismagilov. Theoretical design and analysis of multivolume digital assays with wide dynamic range validated experimentally with microfluidic digital PCR. Anal. Chem. 83: 8158-8168, 2011.

What is claimed is:

1. A computer product comprising a non-transitory computer readable medium storing a plurality of instructions that when executed control a computer system to determine settings for a digital PCR (dPCR) experiment involving pre-amplification of DNA molecules in a plasma sample from a female pregnant with a fetus, the dPCR experiment for the detection of a chromosomal aneuploidy, the instructions comprising:
  receiving data, the data including:
    a number of loci on each of a test chromosome and a control chromosome from which DNA molecules in the plasma sample is to be amplified in a pre-amplification procedure;
    a fetal DNA fraction measured in the plasma sample, the fetal DNA fraction relating to a percentage of DNA molecules in the plasma sample that is fetal in origin;
    a pre-specified fetal DNA fraction error tolerance in a measurement of the fetal DNA fraction;
    a pre-specified error control number that controls a probability that a relative error between an unknown expected fetal DNA fraction and the measured fetal DNA fraction from the plasma sample is within the fetal DNA fraction error tolerance;
    a degree of the chromosomal aneuploidy being tested;
    a pre-specified portion constraint that specifies a portion of DNA molecules resulting from the pre-amplification procedure to be input to the dPCR experiment;
    data about PCR efficiencies for the pre-amplification procedure; and pre-specified error rate criteria for the dPCR experiment including a false positive rate and a false negative rate;
determining a minimal input number of control chromosome molecules for the dPCR experiment based on the pre-specified error rate criteria, the determined fetal DNA fraction, the data about PCR efficiencies, and the degree of chromosomal aneuploidy;
determining a minimal number of control chromosome molecules for the pre-amplification procedure based on the determined fetal DNA fraction, the pre-specified fetal DNA fraction error tolerance, and the pre-specified error control number;
estimating a number of PCR cycles in the pre-amplification procedure based on the minimal input number of control chromosome molecules for the dPCR experiment, the minimal number of control chromosome molecules for the pre-amplification procedure, the data about PCR efficiencies for the pre-amplification procedure, the number of loci for the pre-amplification procedure, and the pre-specified portion constraint;
causing a PCR amplification device to perform the pre-amplification procedure using the determined minimal number of control chromosome molecules for the estimated number of PCR cycles; and
causing a dPCR device to perform the dPCR experiment to detect the chromosomal aneuploidy in the fetal DNA molecules in the plasma sample using the determined minimal input number of control chromosome molecules.

2. The computer product of claim 1, wherein the instructions further comprise:
determining a size of the plasma sample as a volume based on the minimal number of control chromosome molecules for inputting to the pre-amplification procedure.

3. The computer product of claim 2, wherein:
performing the pre-amplification procedure comprises:
inputting the volume of the plasma sample to the PCR amplification device; and
performing the estimated number of PCR cycles on the volume of the plasma sample; and
performing the dPCR experiment comprises:
inputting the portion of DNA molecules resulting from the pre-amplification procedure according to the pre-specified portion constraint to a plurality of partitions of the dPCR device;
performing PCR on the portion of DNA molecules in the plurality of partitions;
determining a first number of positive partitions for DNA fragments from the test chromosome in the plurality of partitions;
determining a second number of positive partitions for DNA fragments from one or more control chromosomes in the plurality of partitions;
determining a test statistic based on the first number of positive partitions and the second number of positive partitions; and
comparing the test statistic to a pre-specified cutoff value to determine whether the fetus has the chromosomal aneuploidy.

4. The computer product of claim 3, wherein the fetal DNA fraction in the plasma sample is measured using a first portion of the plasma sample.

5. The computer product of claim 1, wherein the data about the PCR efficiencies includes at least one of:

a pre-specified lower bound for PCR efficiencies;
an assumption about equal average PCR efficiencies of the test chromosome and the control chromosome; and
PCR efficiency rates for the pre-amplification procedure for a test chromosome and a control chromosome.

6. The computer product of claim 1, wherein the instructions further comprise:
calculating a minimal detectable relative difference for the dPCR experiment using the pre-specified error rate criteria, the determined fetal DNA fraction, and an input number of control chromosome molecules to the dPCR experiment; and
calculating the minimal input number of control chromosome molecules for the dPCR experiment using the minimal detectable relative difference.

7. The computer product of claim 1, wherein calculating the minimal input number of control chromosome molecules for the dPCR experiment is determined by:

$$\hat{\mu}_{pc} = \left(\frac{z_{1-\beta}\sqrt{1+g(h)} + z_{1-\alpha}\sqrt{1+g(1)}}{2(\sqrt{g(h)} - \sqrt{g(1)})}\right)^2 - \frac{3}{8}, \text{ where}$$

$$g(h) = \frac{1}{R}(hf + 1 - f).,$$

where $f$ is the fetal DNA fraction, h is the degree of aneuploidy, R corresponds to a ratio of PCR efficiencies at loci of the control chromosome and the test chromosome, g(1) is the value of g(h) when h=1, $\alpha$ is the false positive rate and $\beta$ is the false negative rate, $z_{1-\alpha}$ is the $100(1-\alpha)\%$ th quantile of the standard Normal distribution, $z_{1-\beta}$ is the $100(1-\beta)\%$ th quantile of the standard Normal distribution.

8. The computer product of claim 7, wherein:

$$R = \frac{\sum_{l=1}^{L_c}(1+y_c^l)^p}{\sum_{l=1}^{L_t}(1+y_t^l)^p},$$

where $L_c$ is the number of loci on one or more control chromosomes, $L_t$ is the number of loci on the test chromosome, p is the number of pre-amplification cycles, and y is a PCR efficiency at a particular locus in the pre-amplification procedure.

9. The computer product of claim 8, wherein R is equal to $$\frac{L_c}{L_t}.$$

10. The computer product of claim 1, wherein calculating the minimal number of control chromosome molecules for the pre-amplification procedure is determined by:

$$\hat{Z}_{0c} = \frac{z_{1-\frac{\eta}{2}}^2}{\psi^2}\left(\frac{1}{f} - 1\right),$$

where $\psi$ is the pre-specified fetal DNA fraction error tolerance, $f$ is the determined fetal DNA fraction, $\eta$ is the pre-specified error control number, and $z_{1-\frac{\eta}{2}}$ is the $$100\left(1-\frac{\eta}{2}\right)\% - th$$

quantile of the standard Normal distribution.

11. The computer product of claim 1, wherein estimating the number of PCR cycles in the pre-amplification procedure is determined by:

$$\hat{p} = \log_{(1+y_0)} \frac{\hat{\mu}_{pc}}{\tau \hat{Z}_{0c} L_c},$$

where $\hat{\mu}_{pc}$ is the minimal input number of control chromosome molecules for the dPCR experiment, $\tau$ is the pre-specified portion constraint, $y_0$ is a lower bound for the PCR efficiency in the pre-amplification procedure, $L_c$ is the number of loci on one or more control chromosomes and equals the number of loci on the test chromosome, and $\hat{Z}_{0c}$ is the minimal number of control chromosome molecules for the pre-amplification procedure.

12. The computer product of claim 1, wherein the fetal DNA fraction error tolerance is 0.05, an error control number is 0.05, and the portion constraint is 0.005.

13. The computer product of claim 1, wherein only one control chromosome among twenty three pairs of human chromosomes is used, wherein a plurality of loci are used on the test chromosome and the control chromosome, and wherein a same number of loci are used on the test chromosome and the control chromosome.

* * * * *